United States Patent
Kristiansen et al.

(10) Patent No.: US 6,590,118 B1
(45) Date of Patent: Jul. 8, 2003

(54) AROMATIC COMPOUNDS

(75) Inventors: Marit Kristiansen, Søborg (DK); Palle Jakobsen, Værløse (DK); Jane Marie Lundbeck, Glostrup (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/672,460

(22) Filed: Sep. 28, 2000

Related U.S. Application Data

(60) Provisional application No. 60/159,261, filed on Oct. 13, 1999.

(30) Foreign Application Priority Data

Sep. 29, 1999 (DK) .......................... 1999 01384

(51) Int. Cl.[7] .................... C07C 255/00; C07C 205/00; C07C 229/00; C07C 63/83; C07F 9/28
(52) U.S. Cl. .......................... 558/416; 560/21; 560/45; 562/11; 562/12; 562/14; 562/433; 562/435; 562/437; 562/488
(58) Field of Search ................................. 562/488, 435, 562/437, 433, 442, 11, 12, 14; 558/416; 560/21, 45

(56) References Cited

U.S. PATENT DOCUMENTS 4,298,215 A    11/1981   Schmidt et al. ............ 282/27.5

FOREIGN PATENT DOCUMENTS

| DE | 42 02 184 A1 | 7/1993 |
|---|---|---|
| DE | 251 550 A1 | 11/1997 |
| FR | 1595520 | 6/1970 |
| GB | 1 427 318 | 3/1976 |
| GB | 1 585 879 | 3/1981 |

OTHER PUBLICATIONS

Frejd et al, A New Rearrangement of N–Arylhydroxamic Acids Catalyzed by Seleninic Acids and Phenylselenyl Chloride, 1978, Tetrahedron Letters , 26, pp. 2239–2242.*

Konieczny et al, 1996, Absence of Noncyclic Amide Formation in PMDA–ODA Polyimide, Macromolecules, 29, pp. 7613–7615.*

Crego, et al. "A Receptor For Aromatic Acids and Amides" Tetrahedron Letters, vol. 33. No. 48, pp. 7437–7440 (1992).

STN International, file CAPLUS, Accession No. 1979:87354–Document No. 90:87354, Wolfgang et al"Synthesis and reactions of bicyclic Sulfuranes" J. Chem. Res. (S) (1978).

Nosova et al Izv. Akad. Nauk SSSR, Ser. Khim., Acylation of Aromatic Aminodicarboxylic Acids, 1987, (8), pp. 1810–1813. English Abstract.*

* cited by examiner

Primary Examiner—Johann Richter
Assistant Examiner—Paul A. Zucker
(74) Attorney, Agent, or Firm—Cheryl H. Agris; Reza Green

(57) ABSTRACT

Disclosed are compounds of formula I

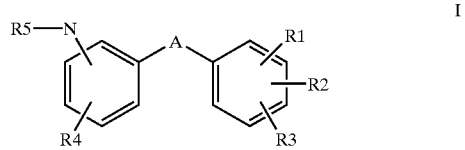

wherein A, R1, R2, R3, R4 and R5 are described in the specification, pharmaceutical formulations comprising these compounds, the use of these compounds are medicaments, the use of these medicaments in the treatment of and/or prevention of diabetes, especially non-insulin dependent diabetes (NIDDM or Type 2 diabetes), as well as methods for treating diabetes comprising administration of these compounds.

9 Claims, No Drawings

AROMATIC COMPOUNDS

CROSS-REFERENCE TO RELATED APPLICATIONS

This application claims priority under 35 U.S.C. 119 of U.S. Provisional Application No. 60/159,261 filed Oct. 13, 1999 and Danish application PA 1999 01384 filed Sep. 29, 1999, the contents of which are fully incorporated herein by reference.

FIELD OF THE INVENTION

The present invention relates to novel compounds, the use of these compounds as medicaments, the use of these medicaments in the treatment of and/or prevention of diabetes, and especially non-insulin dependent diabetes (NIDDM or Type 2 diabetes) including overnight or meal treatment and treatment or prevention of long-term complications, such as retinopathy, neuropathy, nephropathy, and micro- and macroangiopathy; treatment of hyperglycemia, hyperchloesterolemia, hypertension, hyperinsulinemia, hyperlipidemia, atherosclerosis or ischemia or treatment or prophylaxis of obesity or appetite regulation, pharmaceutical compositions containing these compounds and methods of preparing the compounds.

BACKGROUND OF THE INVENTION

Diabetes is characterized by an impaired glucose metabolism manifesting itself among other things by an elevated blood glucose level in the diabetic patients. Underlying defects lead to a classification of diabetes into two major groups: Type 1 diabetes, or insulin demanding diabetes mellitus (IDDM), which arises when patients lack β-cells producing insulin in their pancreatic glands, and Type 2 diabetes, or non-insulin dependent diabetes mellitus (NIDDM), which occurs in patients with an impaired β-cell function besides a range of other abnormalities.

Type 1 diabetic patients are currently treated with insulin, while the majority of Type 2 diabetic patients are treated either with sulphonylureas that stimulate β-cell function or with agents that enhance the tissue sensitivity of the patients towards insulin or with insulin. Among the agents applied to enhance tissue sensitivity towards insulin metformin is a representative example.

Even though sulphonylureas are widely used in the treatment of NIDDM this therapy is, in most instances, not satisfactory: In a large number of NIDDM patients sulphonylureas do not suffice to normalise blood sugar levels and the patients are, therefore, at high risk for acquiring diabetc complications. Also, many patients gradually lose the ability to respond to treatment with sulphonylureas and are thus gradually forced into insulin treatment. This shift of patients from oral hypoglycaemic agents to insulin therapy is usually ascribed to exhaustion of the β-cells in NIDDM patients.

In normal subjects as well as in diabetic subjects, the liver produces glucose in order to avoid hypoglycaemia. This glucose production is derived either from the release of glucose from glycogen stores or from gluconeogenesis, which is a de novo intracellular synthesis of glucose. In Type 2 diabetes, however, the regulation of hepatic glucose output is poorly controlled and is increased, and may be doubled after an overnight fast. Moreover, in these patients there exists a strong correlation between the increased fasting plasma glucose levels and the rate of hepatic glucose production (reviewed in R. A. De Fronzo: *Diabetes* 37, 667–687 (1988); A. Consoli: *Diabetes Care* 15, 430–441 (1992); and J. E. Gerich: *Horm.Metab.Res.* 26, 18–21 (1992)). Similarly, hepatic glucose production will be increased in Type 1 diabetes, if the disease is not properly controlled by insulin treatment.

Since existing forms of therapy of diabetes does not lead to sufficient glycaemic control and therefore are unsatisfactory, there is a great demand for novel therapeutic approaches. Since the liver in diabetes is known to have an increased glucose production, compounds inhibiting this activity are highly desirable. Recently, patent applications on inhibitors of the liver specific enzyme, glucose-6-phosphatase, which is necessary for the release of glucose from the liver, have been filed, for example DE-A-4,202, 183, DE-A-4,202,184, WO98/40385, WO99/40062, and JP-A-4-58565.

Substituted N-(indole-2-carbonyl)-glycinamides acting as glycogen phosphorylase inhibitors are disclosed in WO96/39384, WO96/39385 and in EP-A-0 846 464. Piperidine and pyrrolidine compounds acting as glycogen phosphorylase inhibitors are disclosed in WO95/24391, WO 97/09040, WO 98/40353, and WO 98/50359.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in colour due to the presence of lipid deposits found principally within smooth-muscle cells and in macrophages of the intima layer of the arteries and aorta. Further, it is postulated that most of the chloesterol found within the fatty streaks, in turn, give rise to development of the "fibrous plaque", which consists of accumulated intimal smooth muscle cells laden with lipid and surrounded by extra-cellular lipid, collagen, elastin and proteoglycans. The cells plus matrix form a fibrous cap that covers a deeper deposit of cell debris and more extracellular lipid. The lipid is primarily free and esterified chloesterol. The fibrous plaque forms slowly, and is likely in time to become calcified and necrotic, advancing to the "complicated lesion" which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma chloesterol levels, and low density lipoprotein chloesterol in particular, as an essential step in prevention of CVD. The upper limits of "normal" are now known to be significantly lower than heretofore appreciated. As a result, large segments of Western populations are now realized to be at particular high risk. Independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition, which occurs in the human population as a secondary symptom to various other disorders such as renal artery stenosis, pheochromocytoma, or endocrine disorders. However, hypertension is also evidenced in many patients in whom the causative agent or disorder is unknown. While ushc "essential" hypertension is often associated with disorders such as obesity, diabetes, and hypertriglyceridemia, the relationship between these disorders has not been elucidated. Additionally, many patients display the symptoms of high blood pressure in the complete absence of any other signs of disease or disorder.

It is know that hypertension can directly lead to heart failure, renal failure, and stroke (brain haemorrhaging). These conditions are capable of causing short-term death in a patient. Hypertension can also contribute to the development of atherosclerosis and coronary disease. These conditions gradually weaken a patient and can lead to long-term death.

The exact cause of essential hypertension is unknown, though a number of factors are believed to contribute to the onset of the disease. Among such factors are stress, uncontrolled emotions, unregulated hormone release (the renin, angiotensin aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure, and brain haemorrhaging. However, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemics can prevent abnormal vascular growth and renal sodium retention caused by high insulin levels and thereby alleviates hypertension.

Cardiac hypertrophy is a significant risk factor in the development of sudden death, myocardial infarction, and congestive heart failure. These cardiac events are due, at least in part, to increased susceptibility to myocardial injury after ischemia and reperfusion, which can occur in outpatient as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20–25% in some series. In addition, of the 400,000 patients undergoing coronary by-pass surgery annually, perioperative myocardial infarction is estimated to occur in 5% and death in 1–2%. There is currently no drug therapy in this area, which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients.

Another field for the present invention is obesity or appetite regulation.

Obesity is a well-known risk factor for the development of many very common diseases such as atherosclerosis, hypertension, and diabetes. The incidence of obese people and thereby also these diseases is increasing throughout the entire industrialised world. Except for exercise, diet and food restriction no convincing pharmacological treatment for reducing body weight effectively and acceptably currently exist. However, due to its indirect but important effect as a risk factor in mortal and common diseases it will be important to find treatment for obesity and/or means of appetite regulation.

The term obesity implies an excess of adipose tissue. In this context obesity is best viewed as any degree of excess adiposity that imparts a health risk. The cut off between normal and obese individuals can only be approximated, but the health risk imparted by the obesity is probably a continuum with increasing adiposity. The Framingham study demonstrated that a 20% excess over desirable weight clearly imparted a health risk (Mann G V *N.Eng.J.Med* 291:226, 1974). In the United States a National Institutes of Health consensus panel on obesity agreed that a 20% increase in relative weight or a body mass index (BMI=body weight in kilograms divided by the square of the height in meters) above the 85th percentile for young adults constitutes a health risk. By the use of these criteria 20 to 30 percent of adult men and 30 to 40 percent of adult women in the United State are obese. (NIH, *Ann Intern Med* 103:147, 1985).

Even mild obesity increases the risk for premature death, diabetes, hypertension, atherosclerosis, gallbladder disease, and certain types of cancer. In the industrialised western world the prevalence of obesity has increased significantly in the past few decades. Because of the high prevalence of obesity and its health consequences, its prevention and treatment should be a high public health priority.

When energy intake exceeds expenditure, the excess calories are stored in adipose tissue, and if this net positive balance is prolonged, obesity results, i.e. there are two components to weight balance, and an abnormality on either side (intake or expenditure) can lead to obesity.

The regulation of eating behaviour is incompletely understood. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding centre that stimulate eating, and the satiety centre modulates this process by sending inhibitory impulses to the feeding centre. Several regulatory processes may influence these hypothalamic centres. The satiety centre may be activated by the increases in plasma glucose and/or insulin that follow a meal. Meal-induce gastric distension is another possible inhibitory factor. Additionally the hypothalamic centres are sensitive to catecholamines, and beta-adrenergic stimulation inhibits eating behaviour. Ultimately, the cerebral cortex controls eating behaviour, and impulses from the feeding centre to the cerebral cortex are only one input. Psychological, social, and genetic factors also influence food intake.

At present a variety of techniques are available to effect initial weight loss. Unfortunately, initial weight loss is not an optimal therapeutic goal. Rather, the problem is that most obese patients eventually regain their weight. An effective means to establish and/or sustain weight loss is the major challenge in the treatment of obesity today.

Thus there remains today a need in the art for compositions and methods that are useful for the treatment or prophylaxis of obesity or appetite regulation.

OBJECTS AND SUMMARY OF THE INVENTION

One object of the present invention is to provide compounds that can be used as medicaments for treatment of one or more of the above-mentioned diseases and disorders.

A further object of this invention is to provide compounds that can effectively be used in the treatment of diabetes, preferably Type 2 diabetes, including overnight or meal treatment and preferably for treatment of increased plasma glucose levels.

A still further object of this invention is to provide compounds that can effectively be used as inhibitors of glucose production from the liver.

A still further object of this invention is to provide compounds that can be effectively used as glycogen phosphorylase inhibitors.

It has now been found that members of a novel group of aromatic compounds with formula I have interesting pharmacological properties. For example, the compounds of this invention can be used in the treatment of diabetes. Especially, the compounds of this invention are active as inhibitors of glucose production from the liver. Consequently, the compounds of this invention can be used for the treatment of the increased plasma glucose levels in diabetics.

Accordingly, it is an object of the present invention to provide such novel compounds.

Further objects will become apparent from the following description.

DETAILED DESCRIPTION OF THE INVENTION

The present invention relates to novel compounds of the general formula I

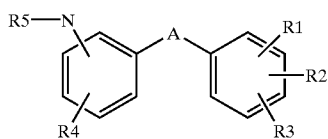

I as well as any optical or geometric isomer or tautomeric form thereof including mixtures of these or pharmaceutically acceptable basic organic or inorganic addition salts or hydrates or prodrugs thereof, wherein A is —O—, —S—, >SO, >SO$_2$, >CO, >CR9R10, or >NR11;

R1 and R2 independently are one of the following groups: hydrogen, CN, —C(O)NR6R7, —COOH, —PO(OH)$_2$, —SO$_2$OH, tetrazole, 1-hydroxy-1,2-diazole, 1-hydroxytriazole, 1-hydroxyimidazole, 2-hydroxytriazole, or 1-hydroxytetrazole; when R1 or R2 is hydrogen, the other of R1 and R2 is —PO(OH)$_2$ or —SO$_2$OH; or R1 and R2 together may form an anhydride or an imide;

R3 and R4 independently are C$_{1-8}$-alkyl, C$_{2-8}$-alkenyl, C$_{2-8}$-alkynyl, or C$_{3-8}$-cycloalkyl, each optionally substituted with halogen, hydroxy, —SH, —SOR6, —SO$_2$R6, —NR6R7, —NHCOR7, C$_{1-8}$-alkoxy, NO$_2$, trifluoromethoxy, carbamoyl, or —CONR6R7; or R3 and R4 independently are hydrogen, halogen, perhalomethyl, C$_{1-8}$-alkoxy, C$_{1-8}$-alkylthio, —SH, —SOR6, —SO$_2$R6, trifluoromethoxy, —SO$_2$OH, —PO(OH)$_2$, —COOR6, —CN, hydroxy, —OCOR6, —NR6R7, —NHCOR7, —COC$_{1-8}$-alkyl, —CONR6R7, —CONHSO$_2$R7, —SO$_2$NHR7, NO$_2$, C$_{1-8}$alkoxycarbonyl, aryl, heteroaryl, C$_{1-8}$-alkylphenyl, or tetrazole;

R5 is —CO—R8, —CH$_2$—R8, or —CS—R8; wherein R8 is aryl, C$_{1-8}$alkyl, C$_{2-8}$-alkene, phenyl-C$_{1-8}$alkyl, heteroaryl, or C$_{3-8}$-cycloalkyl, each optionally substituted with one or more substituents selected from halogen, hydroxy, —SH, —SOR6, —SO$_2$R6, NO$_2$, —NR6R7, —NYCOR7, C$_{1-8}$-alkyl, C$_{1-8}$-alkoxy, perhalomethoxy, carbamoyl, —CONR6R7, perhalomethyl, —OCOR6, —CO—R6, —OR6, C$_{1-8}$-alkylthio, —COOR6, —SO$_2$OH, —SO$_2$CH$_3$, —PO(OH)$_2$, —CN, —NHCOR7, —CONHSO$_2$R7, —SO$_2$NHR7, C$_{1-8}$-alkoxycarbonyl, and tetrazole; wherein R6 and R7 independently are hydrogen, C$_{1-8}$-alkyl, aryl, phenyl-C$_{1-8}$-alkyl or heteroaryl, each optionally substituted with one or more substituents selected from halogen, OH, NH$_2$, NO$_2$, —NH(C$_{1-8}$-alkyl), —N(C$_{1-8}$-alkyl)$_2$, —NHCO(C$_{1-8}$-alkyl), C$_{1-8}$-alkoxy, and trifluoromethoxy;

R9 and R10 independently are hydrogen, hydroxy, SH, halogen, or C$_{1-8}$-alkyl; and R11 is hydrogen, C$_{1-8}$-alkyl, -carbonyl(C$_{1-8}$-alkyl), or phenyl-C$_{1-8}$-alkyl.

In one embodiment of the present invention A is —O— or —S—, preferably A is —O—.

In a second embodiment of the present invention R1 and R2 both are —COOH or CN, preferably —COOH or R1 and R2 together form an imide.

In a third embodiment of the present invention R3 is hydrogen.

In a further embodiment of the present invention R4 is hydrogen.

In one embodiment of the present invention R5 is —CO—R8, wherein R8 is aryl, C$_{1-8}$-alkyl, C$_{2-8}$-alkene, phenyl-C$_{1-8}$alkyl, heteroaryl, or C$_{3-8}$-cycloalkyl, each optionally substituted with one or more substituents selected from halogen, hydroxy, —SH, —SOR6, —SO$_2$R6, NO$_2$, —NR6R7, —NHCOR7, C$_{1-8}$-alkyl, C$_{1-8}$-alkoxy, perhalomethoxy, carbamoyl, —CONR6R7, perhalomethyl, —OCOR6, —CO—R6, —OR6, C$_{1-8}$alkylthio, —COOR6, —SO$_2$OH, —PO(OH)$_2$, —CN, —NHCOR7, —CONHSO$_2$R7, —SO$_2$NHR7, C$_{1-8}$-alkoxycarbonyl, and tetrazole; wherein R6 and R7 independently are hydrogen, C$_{1-8}$-alkyl, aryl, phenyl-C$_{1-8}$-alkyl or heteroaryl, each optionally substituted with one or more substituents selected from halogen, OH, —SH, —SOR6, —SO$_2$R6, NO$_2$, NH$_2$, NH(C$_{1-8}$-alkyl), N(C$_{1-8}$-alkyl($_2$, NHCO(C$_{1-8}$-alkyl), C$_{1-8}$-alkoxy, and trifluoromethoxy.

In a second embodiment of the present invention R5 is —CO—R8, wherein R8 is aryl or hetereoaryl, each optionally substituted with one or more substituents selected from halogen, hydroxy, —SH, —SOR6, —SO$_2$R6, NO$_2$, —NR6R7, —NHCOR7, $C_{1-8}$-alkyl, $C_{1-8}$-alkoxy, perhalomethoxy, carbamoyl, —CONR6R7, perhalomethyl, —OCOR6, —CO—R6, —OR6, $C_{1-8}$-alkylthio, —COOR6, —SO$_2$OH, —PO(OH)$_2$, CN, —NHCOR7, —CONHSO$_2$R7, —SO$_2$NHR7, $C_{1-8}$-alkoxycarbonyl, and tetrazole; wherein R6 and R7 independently are hydrogen, $C_{1-8}$-alkyl, aryl, phenyl-$C_{1-8}$-alkyl or heteroaryl, each optionally substituted with one or more substituents selected from halogen, OH, —SH, —SOR6, —SO$_2$R6, NO$_2$, NH$_2$, —NH($C_{1-8}$-alkyl), —N($C_{1-8}$-alkyl)$_2$, —NHCO($C_{1-8}$-alkyl), $C_{1-8}$-alkoxy, and trifluoromethoxy.

In a third embodiment of the present invention R5 is —CO—R8, wherein R8 is aryl (preferably phenyl) optionally substituted with one or more substituents selected from halogen, hydroxy, —SH, —SOR6, —SO$_2$R6, NO$_2$, —NR6R7, —NHCOR7, $C_{1-8}$-alkyl, $C_{1-8}$-alkoxy, perhalomethoxy, carbamoyl, —CONR6R7, perhalomethyl, —OCOR6, —CO—R6, —OR6, $C_{1-8}$-alkylthio, —COOR6, —SO$_2$OH, —PO(OH)$_2$, CN, —NHCOR7, —CONHSO$_2$R7, —SO$_2$NHR7, $C_{1-8}$-alkoxycarbonyl, and tetrazole; wherein R6 and R7 independently are hydrogen, $C_{1-8}$-alkyl, aryl, phenyl-$C_{1-8}$-alkyl or heteroaryl, each optionally substituted with one or more substituents selected from halogen, OH, NH$_2$, —SH, —SOR6, —SO$_2$R6, NO$_2$, —NH($C_{1-8}$-alkyl), —N($C_{1-8}$-alkyl)$_2$, —NHCO($C_{1-8}$-alkyl), $C_{1-8}$-alkoxy, and trifluoromethoxy.

In a further embodiment of the present invention R5 is —CO—R8, wherein R8 is aryl (preferably phenyl) optionally substituted with one or more substituents selected from halogen, COOR6, NO$_2$, —SO$_2$CH$_3$, CN, $C_{1-8}$-alkyl (preferably methyl, tert-butyl, isopropyl, pentyl, heptyl), perhalomethyl (preferably trifluoromethyl), $C_{1-8}$-alkoxy (preferably methoxy or ethoxy), perhalomethoxy (preferably trifluoromethoxy), $C_{1-8}$-alkylthio (preferably methylthio), —CO—R6, —NR6R7, —NH—CO—R7, and —OR6; wherein R6 and R7 independently are hydrogen, $C_{1-8}$-alkyl, aryl, phenyl-$C_{1-8}$-alkyl or heteroaryl, each optionally substituted with one or more substituents selected from halogen, OH, NH$_2$, —SH, —SOR6, —SO$_2$R6, NO$_2$, —NH($C_{1-8}$-alkyl), —N($C_{1-8}$alkyl)$_2$, —NHCO($C_{1-8}$alkyl), $C_{1-8}$-alkoxy, and trifluoromethoxy.

In a still further embodiment of the present invention R5 is —CO—R8, wherein R8 is aryl (preferably phenyl) optionally substituted with one or more substituents and at least one of the substituents is COOH.

In a still further embodiment of the present invention R5 is —CO—R8, wherein R8 is aryl (preferably phenyl) optionally substituted with one or more substituents and at least one of the substituents is NO$_2$.

In a still further embodiment of the present invention R5 is —CO—R8, wherein R8 is aryl (preferably phenyl) optionally substituted with one or more substituents and at least one of the substituents is halogen (preferably bromo or chloro).

In a further embodiment of the present invention R5 is —CO—R8, wherein R8 is aryl (preferably phenyl) substituted with one or more substituents and at least one of the substituents is —CO—R6, wherein R6 is $C_{1-8}$-alkyl (preferably CH$_3$) or substituted aryl (preferably phenyl) substituted with halogen or substituted with $C_{1-8}$-alkyl (preferably CH$_3$).

In one embodiment of the present invention R5 is —CO—R8, wherein R8 is aryl (preferably phenyl) substituted with one or more substituents and at least one of the substituents is —NH—CO—R7, wherein R7 is $C_{1-8}$-alkyl (preferably CH$_3$).

In a second embodiment of the present invention R5 is —CO—R8, wherein R8 is aryl (preferably phenyl) substituted with one or more substituents and at least one of the substituents is —NR6R7, wherein R6 and R7 independently are hydrogen or $C_{1-8}$-alkyl (preferably CH$_3$).

In a third embodiment of the present invention R5 is —CO—R8, wherein R8 is phenyl substituted with one or more substituents and at least one of the substituents is —OR6, wherein R6 is $C_{1-8}$-alkyl (preferably methyl).

In a further embodiment of the present invention R5 is —CO—R8, wherein R8 is benzo[1,3]dioxole, 2,3-dihydrobenzofuran, or benzofuran, each optionally substituted with one or more substituents selected from halogen, $C_{1-8}$-alkyl (preferably methyl), and $C_{1-8}$-alkoxy (preferably methoxy).

The present invention relates also to novel compounds of the general formula I*a*

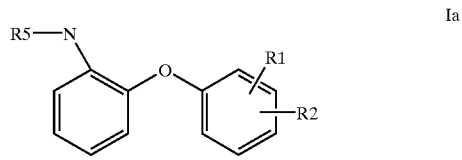

wherein

R1 and R2 independently are one of the following groups: hydrogen, CN, —C(O)NR6R7, —COOH, —PO(OH)$_2$, —SO$_2$OH, tetrazole, 1-hydroxy-1,2-diazole, 1-hydroxytriazole, 1-hydroxyimidazole, 2-hydroxytriazole, 1-hydroxytetrazole; when R1 or R2 is hydrogen, the other of R1 and R2 is —PO(OH)$_2$ or —SO$_2$OH; or R1 and R2 together may form an anhydride or an imide;

R5 is —CO—R8, —CH$_2$—R8, or —CS—R8; wherein R8 is aryl, $C_{1-8}$-alkyl, $C_{2-8}$-alkene, phenyl-$C_{1-8}$-alkyl, hetereoaryl, or $C_{3-8}$-cycloalkyl, each optionally substituted with one or more substituents selected from halogen, hydroxy, —SH, —SOR6, —SO$_2$R6, NO$_2$, —NR6R7, —NHCOR7, $C_{1-8}$-alkyl, $C_{1-8}$-alkoxy, perhalomethoxy, carbamoyl, —CONR6R7, perhalomethyl, —OCOR6, —CO—R6, —OR6, $C_{1-8}$-alkylthio, —COOR6, —SO$_2$OH, —PO(OH)$_2$, —CN, —NHCOR7, —CONHSO$_2$R7, —SO$_2$NHR7, $C_{1-8}$-alkoxycarbonyl, and tetrazole;

wherein R6 and R7 independently are hydrogen, $C_{1-8}$-alkyl, aryl, phenyl-$C_{1-8}$-alkyl, or heteroaryl, each optionally substituted with one or more substituents selected from halogen, OH, NH$_2$, —SH, —SOR6, —SO$_2$R6, NO$_2$, —NH($C_{1-8}$-alkyl), —N($C_{1-8}$-alkyl)$_2$, —NHCO($C_{1-8}$-alkyl), $C_{1-8}$-alkoxy, and trifluoromethoxy.

In a preferred embodiment of the present invention R1 and R2 are —COOH.

In another preferred embodiment of the present invention R5 is —CO—R8, wherein R8 is aryl, $C_{1-8}$-alkyl, $C_{2-8}$-alkene, phenyl-$C_{1-8}$-alkyl, heteroaryl, or $C_{3-8}$-cycloalkyl, each optionally substituted with one or more substituents selected from halogen, hydroxy, —SH, —SOR6, —SO$_2$R6, NO$_2$, —NR6R7, —NHCOR7, $C_{1-8}$-alkyl, $C_{1-8}$-alkoxy, perhalomethoxy, cabamoyl, —CONR6R7, perhalomethyl, —OCOR6, —CO—R6, —OR6, $C_{1-8}$-alylthio, —COOR6, —SO$_2$OH, —PO(OH)$_2$, —CN, —NHCOR7, —CONHSO$_2$R7, —SO$_2$NHR7, $C_{1-8}$-alkoxycarbonyl, and tetrazole; wherein R6 and R7 independently are hydrogen, $C_{1-8}$-alkyl, aryl, phenyl-$C_{1-8}$-alkyl or heteroaryl, each optionally substituted with one or more substituents selected from halogen, OH, NH$_2$, —SH, —SOR6, —SO$_2$R6, NO$_2$, —NH($C_{1-8}$-alkyl), —N($C_{1-8}$-alkyl)$_2$, —NHCO($C_{1-8}$alkyl), $C_{1-8}$-alkoxy, and trifluoromethoxy.

The present invention also relates to novel compounds of the general formula Ib

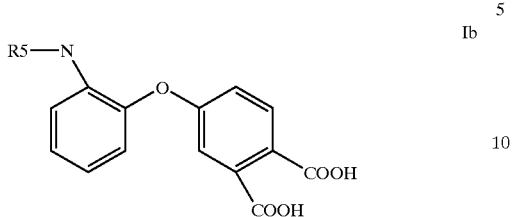

Ib wherein R5 is —CO—R8, wherein R8 is aryl, $C_{1-8}$-alkyl, $C_{2-8}$-alkene, phenyl-$C_{1-8}$-alkyl, heteroaryl, or $C_{3-8}$-cycloalkyl, each optionally substituted with one or more substituents selected from halogen, hydroxy, —SH, —SOR6, —SO$_2$R6, NO$_2$, —NR6R7, —NHCOR7, $C_{1-8}$-alkyl, $C_{1-8}$-alkoxy, perhalomethoxy, carbamoyl, —CONR6R7, perhalomethyl, —OCOR6, —CO—R6, —OR6, $C_{1-8}$-alkylthio, —COOR6, —SO$_2$OH, —PO(OH)$_2$, —CN, —NHCOR7, —CONHSO$_2$R7, —SO$_2$NHR7, $C_{1-8}$-alkoxycarbonyl, and tetrazole; wherein R6 and R7 independently are hydrogen, $C_{1-8}$-alkyl, aryl, pheny-$C_{1-8}$-alkyl, or heteroaryl, each optionally substituted with one or more substituents selected from halogen, OH, NH$_2$, —SH, —SOR6, —SO$_2$R6, NO$_2$, —NH($C_{1-8}$-alkyl), —N($C_{1-8}$-alkyl)$_2$, —NHCO($C_{1-8}$-alkyl), $C_{1-8}$-alkoxy, and trifluoromethoxy.

Preferably R5 is —CO—R8, wherein R8 is aryl (preferably phenyl) optionally substituted with one or more substituents selected from halogen, COOR6, NO$_2$, —SO$_2$CH$_3$, CN, $C_{1-8}$-alkyl (preferably methyl, tertbutyl, isopropyl, pentyl, heptyl), perhalomethyl (preferably trifluoromethyl), $C_{1-8}$-alkoxy (preferably methoxy or ethoxy), perhalomethoxy (preferably trifluoromethoxy), $C_{1-8}$-alkylthio (preferably methylthio), —CO—R6, —NR6R7, —NH—CO—R7, and —OR6; wherein R6 and R7 independently are hydrogen, $C_{1-8}$-alkyl, aryl, phenyl-$C_{1-8}$-alkyl or heteroaryl, each optionally substituted with one or more substituents selected from halogen, OH, NH$_2$, —SH, —SOR6, —SO$_2$R6, NO$_2$, —NH($C_{1-8}$-alkyl), —N($C_{1-8}$-alkyl)$_2$, —NHCO($C_{1-8}$-alkyl), $C_{1-8}$-alkoxy, and trifluoromethoxy.

Preferred compounds of the present invention are:
4-[2-(3-dimethylaminobenzoylamino)phenoxy]phthalic acid, 4-[2-(3-dimethylaminobenzoyl-amino)phenoxy]phthalic acid dimethyl ester, 4-[2-(3-iodobenzoylamino)phenoxy]phthalic acid, 4-[2-(3-iodobenzoylamino)phenoxy]phthalic acid dimethyl ester, 4-[2-(2-fluoro-5-trifluoromethylbenzoylamino)phenoxy]phthalic acid, 4-[2-(2-fluoro-5-trifluoromethylbenzoyl-amino)phenoxy]phthalic acid dimethyl ester, 4-[2-(2-fluorobenzoylamino)phenoxy]phthalic acid, 4-[2-(2-fluorobenzoylamino)phenoxy]phthalic cid dimethyl ester, 4-[2-(3-acetylbenzoyl-amino)phenoxy]phthalic acid, 4-[2-(3-acetylbenzoylamino)phenoxy]phthalic acid dimethyl ester, 4-[2-(3-bromobenzoylamino)phenoxy]phthalic acid, 4-[2-(3-bromobenzoylamino)-phenoxy]phthalic acid dimethyl ester, 4-[2-(3-chlorobenzoylamino)phenoxy]phthalic acid 4-[2-(3-chlorobenzoylamino)phenoxy]phthalic acid dimethyl ester, 4-[2-(2,3-difluorobenzoyl-amino)phenoxy]phthalic acid, 4-[2-(2,3-difluorobenzoylamino)phenoxy]phthalic acid dimethyl ester, 4-[2-(2,4-difluorobenzoylamino) phenoxy]phthalic acid, 4-[2-(2,4-difluorobenzoylamino)-phenoxy]phthalic acid dimethyl ester, 4-[2-(2,5-difluorobenzoylamino)phenoxy] phthalic aicd, 4-[2-(2,5-difluorobenzoylamino) phenoxy]phthalic aicd dimethyl ester, 4-[2-(4-fluorobenzoyl-amino)phenoxy]phthalic acid, 4-[2-(4-fluorobenzoylamino)phenoxy]phthalic acid dimethyl ester, 4-(2-benzoylaminophenoxy)phthalic acid, 4-(2-benzoylaminophenoxy)phthalic acid dimethyl ester, 4-[2-(3-methylbenzoylamino)phenoxy]phthalic acid, 4-[2-(3-methylbenzoyl-amino)phenoxy]phthalic acid dimethyl ester, 4-[2-(3-cyanobenzoylamino)phenoxy] phthalic acid, 4-[2-(3-cyanobenzoylamino)phenoxy] phthalic acid dimethyl ester, 4-[4-amino-2-(3-nitrobenzoylamino)phenoxy]phthalic acid, 4-[4-amino-2-(3-nitrobenzoylamino)phenoxy]phthalic acid dimethyl ester, N-[2-(1,3-dioxo-2,3-dihydro-1H-isoindol-5-yloxy)phenyl]-3-nitrobenz-amide, 4-[2-(3-aminobenzoylamino)phenoxy]phthalic acid 4-[2-(3-aminobenzoylamino)-phenoxy]phthalic acid dimethyl ester, 4-[4-(3-nitrobenzoylamino)phenoxy]phthalic acid, 4-[4-(3-nitrobenzoylamino)phenoxy]phthalic acid dimethyl ester, 4-[2-(3-nitrobenzoylamino)-phenylsulphenyl]phthalic acid, 4-[2-(3-nitrobenzoylamino)phenylsulphenyl]phthalic acid dimethyl ester, 4-[2-(3-nitrobenzoylamino)phenoxy] phthalic acid, 4-[2-(3-nitrobenzoylamino)-phenoxy] phthalic acid dimethyl ester, 4-[4-(4-iodobenzoylamino)-2-(3-nitrobenzoylamino)-phenoxy]phthalic acid, 4-[4-(4-iodobenzoylamino)-2-(3-nitrobenzoylamino)phenoxy]phthalic acid dimethyl ester, 4-[4-methoxycarbonyl-2-(3-nitrobenzoylamino) phenoxy]phthalic acid, 4-[4-methoxycarbonyl-2-(3-nitrobenzoylamino)phenoxy]phthalic acid dimethyl ester 4-[4-acetylamino-2-(3-nitrobenzoylamino) phenoxy]phthalic acid, 4-[4acetylamino-2-(3-nitrobenzoylamino)phenoxy]phthalic acid dimethyl ester, 4-[5-fluoro-2-(3-nitrobenzoylamino)-phenoxy]phthalic aicd, 4-[5-fluoro-2-(3-nitrobenzoylamino)phenoxy] phthalic acid dimethyl ester, 4-[4-bromo-2-(3-nitrobenzoylamino)phenoxy]phthalic acid, 4-[4-bromo-2-(3-nitro-benzoylamino)phenoxy]phthalic acid dimethyl ester, 4-[4-benzoylamino-2-(3-nitrobenzoyl-amino)phenoxy]phthalic acid, 4-[4-benzoylamino-2-(3-nitrobenzoylamino)phenoxy] phthalic acid dimethyl ester, 4-[5-methyl-2,4-bis-(3-nitrobenzoylamino)phenoxy]phthalic acid, 4-[5-methyl-2,4-bis-(3-nitrobenzoylamino)phenoxy] phthalic aicd dimethyl ester, 4-[4-cyano-2-(3-nitrobenzoylamino)phenoxy]phthalic acid, 4-[4-cyano-2-(3-nitrobenzoylamino)phenoxy]-phthalic acid dimethyl ester, 4-[4,5-dichloro-2-(3-nitrobenzoylamino)phenoxy]phthalic acid, 4-[4,5-dichloro-2-(3-nitrobenzoylamino)phenoxy]phthalic acid dimethyl ester, 4-[5-bromo-4-fluoro-2-(3-nitrobenzoylamino)phenoxy]phthalic acid, (4-[5-bromo-4-fluoro-2-(3-nitrobenzoyl-amino)phenoxy] phthalic acid dimethyl ester, 4-[4-methyl-2-(3-nitrobenzoylamino)phenoxy]-phthalic acid, 4-[4-methyl-2-(3-nitrobenzoylamino)phenoxy]phthalic acid dimethyl ester, 4-[4-fluor-2-(3-nitrobenzoylamino) phenoxy]phthalic acid, 4-[4-fluoro-2-(3-nitrobenzoylamino)-phenoxy]phthalic acid dimethyl ester, 4-[5-methyl-2-(3-nitrobenzoylamino)phenoxy] phthalic acid, 4-[5-methyl-2-(3-nitrobenzoylamino) phenoxy]phthalic aicd dimethyl ester, 4-[2-(3-nitrobenzoylamino)-4-trifluoromethylphenoxy]phthalic acid, 4-[2-(3-nitrobenzoylamino)-4-trifluoromethylphenoxy]phthalic acid dimethyl ester, 4-[2,4-bis-(3-nitrobenzoylamino)phenoxy]-phthalic acid, 4-[2,4-bis-(3-nitrobenzoylamino)phenoxy]phthalic acid dimethyl ester, 4-[2-(3-nitrobenzoylamino)benzyl] phthalic acid, 4-[2-(3-nitrobenzoylamino)benzyl] phthalic acid dimethyl ester, 4-[2-(3-fluorobenzoylamino)phenoxy]phthalic acid, 4-[2-(3-fluorobenzoyl-amino)phenoxy]phthalic acid dimethyl ester, 4-[2-(3-trifluoromethylbenzoylamino)phenoxy]-phthalic acid, 4-[2-(3-trifluoromethylbenzoylamino) phenoxy]phthalic acid dimethyl ester, 4-[2-(3-nitrobenzylamino)phenoxy]phthalic acid, 4-[2-(3-nitrobenzylamino)phenoxy]phthalic acid dimethyl ester, 4-[2-(3-trifluoromethoxybenzoylamino) phenoxy]phthalic acid, 4-[2-(3-trifluoromethoxybenzoylamino)phenoxy]phthalic acid dimethyl ester, 4{benzyl-[2-(3nitrobenzoyl-amino)phenyl] amino}phthalic acid, 4{benzyl-[2-(3-nitrobenzoylamino)phenyl]amino}phthalic acid dimethyl ester, 4-[2-(3-nitrobenzoylamino)phenoxy] phthalic acid, 4-[2-(3-nitrobenzoyl-amino)phenoxy] phthalic acid dimethyl ester, 4-[2-(3-methoxybenzoylamino)phenoxy]phthalic acid, and 4-[2-(3-methoxybenzoylamino)phenoxy]phthalic acid dimethyl ester.

The compounds of the present invention may have one or more asymmetric centers and it is intended that steroisomers (optical isomers), as separated, pure or partially purified stereoisomers or racemic mixtures thereof are included in the scope of the present invention.

Within the present invention, the compounds of formula I, Ia or Ib may optionally be prepared in the form of pharmaceutically acceptable basic salts or mixtures thereof, as pharmaceutically acceptable metals salts or—optionally alkylated—ammonium salts.

Examples of such salts include inorganic and organic basic addition salts and the like, and include bases related to the pharmaceutically acceptable salts listed in *Journal of Pharmaceutical Science* 66, 2 (1977) and incorporated herein by reference, or lithium, sodium, potassium, magnesium and the like. The compounds of formula I, Ia or Ib may be administered in pharmaceutically acceptable basic addition salt form or, where appropriate, as a alkali metal or alkaline earth metal or lower alkylammonium salt. Such salt forms are believed to exhibit approximately the same order of activity as the free acid forms.

Also intended as pharmaceutically acceptable addition salts are the hydrates, which the present compounds are able to form.

The basic addition salts may be obtained s the direct products of compound synthesis. In the alternative, the free acid may be dissolved in a suitable solvent containing the appropriate base, and the salt isolated by evaporating the solvent or otherwise separating the salt and solvent.

The compounds of this invention may form solvates with standard low molecular weight solvents using methods known to the skilled artisan. Such solvates are also contamplated as being within the scope of the present invention.

The present invention relates to a compound of the above general formula I, Ia or Ib) or a pharmaceutically acceptable salt or prodrug or hydrate thereof or any optical isomer thereof or a mixture of optical isomers, including a racemic mixture, or any tautomeric form thereof for use as a medicament.

The present invention relates to a pharmaceutical composition comprising, as an active ingredient, an effective amount of a compound of the above general formula (I, Ia or Ib) or a pharmaceutically acceptable salt or prodrug or hydrate thereof or any optical isomer thereof, mixture of optical isomers, including a racemix mixture, or any tautomeric form thereof together with a pharmaceutically acceptable carrier or diluent.

In another aspect, the present invention relates to a method for the treatment of diabetes, preferably Type 2 diabetes, the method comprising administering to a subject in need thereof an effective amount of a compound of formula (I, Ia or Ib) or a pharmaceutically acceptable salt or prodrug or hydrate thereof, or of a composition according to the present invention.

In a still further aspect, the present invention relates to a method for the treatment of glycogen phosphorylase dependent diseases the method comprising administering to a subject in need thereof an effective amount of a compound of formula (I, Ia or Ib) or a pharmaceutically acceptable salt or prodrug or hydrate thereof, or of a composition according to the present invention.

In still another aspect, the present invention relates to a method for inhibition of glucose production from the liver, the method comprising administering to a subject in need thereof an effective amount of a compound of formula (I, Ia or Ib) or a pharmaceutically acceptable salt or prodrug or hydrate thereof, or of a composition according to the present invention.

In still another aspect, the present invention relates to a method for the treatment or prophylaxis of obesity or appetite regulation, the method comprising administering to a subject in need thereof an effective amount of a compound of formula (I, Ia or Ib) or a pharmaceutically acceptable salt or prodrug or hydrate thereof, or of a composition according to the present invention.

In still another aspect, the present invention relates to the use of a compound of formula (I, Ia or Ib) or a pharmaceutically acceptable salt or prodrug or hydrate thereof for the preparation of a medicament.

Furthermore the present invention relates to the use of a compound of formula (I, Ia or Ib) or a pharmaceutically acceptable salt of prodrug or hydrate thereof for the preparation of a medicament for the treatment or prevention of diabetes, preferably Type 2 diabetes.

More particular the present invention relates to the use of a compound of formula (I, Ia or Ib) or a pharmaceutically acceptable salt or prodrug or hydrate thereof for the preparation of a medicament for inhibiting the glucose production from the liver.

The present invention relates furthermore to the use of a compound of formula (I, Ia or Ib) or a pharmaceutically acceptable salt or prodrug or hydrate thereof for the preparation of a medicament for inhibiting liver glycogen phosphorylase.

The present invention relates furthermore to the use of a compound of formula (I, Ia or Ib) or a pharmaceutically acceptable salt or prodrug or hydrate thereof for the preparation of a medicament for the treatment or prophylactic of obesity or appetite regulation.

The present invention relates furthermore to the use of a compound of formula (I, Ia or Ib) or a pharmaceutically acceptable salt thereof for the preparation of a medicament for the treatment of hyperglycemia, hyperchloesterolemia, hyperinsulinemia, atherosclerosis, hyperlipidemia or hypertension.

The term "treatment" as used herein is intended to include prophylacit treatment.

DEFINITIONS

In the structural formulas given herein and throughout the present specification, the following terms have the indicated meaning:

The term "optionally substituted" as used herein means that the group in question is either unsubstituted or substituted with one or more of the substituents specified. When the group in question are substituted with more than one substituent the substituent may be the same or different.

The term "halogen" means fluorine, chlorine, bromine or iodine.

The term "perhalomethyl" means trifluoromethyl, trichloromethyl, tribromomethyl, or triiodomethyl.

The term "$C_{1-8}$-alkyl" as used herein, alone or in combination, refers to a straight or branched, saturated hydrocarbon chain having the indicated number of carbon atoms such as e.g. methyl, ethyl, n-propyl, isoproyl, n-butyl, sec-butyl, isobutyl, tert-butyl, n-pentyl, 2-methylbutyl, 3-methylbutyl, 4-methylpentyl, neopentyl, n-pentyl, n-hexyl, 1,2-dimethylpropyl, 2,2-dimethylpropyl, 1,2,2-trimethylpropyl and the like. The term "$C_{1-8}$-alkyl" as used herein also includes secondary $C_{3-8}$-alkyl and tertiary $C_{4-8}$-alkyl.

The term "$C_{2-8}$-alkenyl" as used herein alone or in combination represents a straight or branched hydrocarbon group containing from 2 to the specified number of carbon atoms and at least one double bond. Typical $C_{2-8}$-alkenyl groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-penten;yl, 3-pentenyl, 4-pentenyl, 3-methyl-2-butenyl, 1-hexenyl, 2-hexenyl, 3-hexenyl, 2,4-hexadienyl, 5-hexenyl and the like.

The term "$C_{2-8}$-alkynyl" as used herein alone or in combination, represents a straight or branched hydrocarbon group containing from 2 to the specified number of carbon atoms and at least one triple bond. Examples of "$C_{2-8}$-alkynyl" groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 1-hexynyl, 2-hexynyl, 3-hexynyl, 5-hexynyl, 2,4-hexadiynyl and the like.

The term "$C_{3-8}$-cycloalkyl" as used herein represents a carbocyclic group having from 3 to 8 carbon atoms. typical $C_{3-8}$-cycloalkyl groups include, but are not limited to, cyclopropyl, cyclobutyl, cyclopentyl, cyclohexyl, cycloheptyl, cyclooctyl and the like.

The term "$C_{1-8}$-alkoxy" as used herein, alone or in combination, refers to the radical —O—$C_{1-8}$-alkyl where $C_{1-8}$-alkyl is as defined above. Typical $C_{1-8}$-alkoxy groups include, but are not limited to, methoxy, ethoxy, n-propoxy, isopropoxy, butoxy, sec-butoxy, tert-butoxy, pentoxy, isopentoxy, hexoxy, isohexoxy and the like.

The term "$C_{1-8}$-alkylthio" as used herein, alone or in combination, refers to a straight or branched monovalent substituent comprising a lower alkyl group linked through a divalent sulphur atom having its free valence bond from the sulphur atom and having 1 to 8 carbon atom such as e.g. methylthio, ethylthio, propylthio, butylthio, pentylthio, hexylthio and the like.

The term "$C_{1-8}$-alkoxycarbonyl" as used herein refers to a monovalent substituent comprising a $C_{1-8}$-alkoxy group linked through a carbonyl group; such as e.g. methoxycarbonyl, ethoxycarbonyl, propoxycarbonyl, isopropoxycarbonyl, n-butoxycarbonyl, sec-butoxycarbonyl, tertbutoxycarbonyl, 3-methylbutoxycarbonyl, n-hexoxycarbonyl and the like.

The term "phenyl-$C_{1-8}$-alkyl" as used herein refers to a straight or branched saturated carbin chain containing from 1 to 8 carbon substituted with phenyl; such as e.g. benzyl, phenylethyl, 3-phenylpropyl and the like.

The term "$C_{1-8}$-alkylphenyl" as used herein refers to phenyl substituted by $C_{1-8}$-alkyl as defined above.

The term "carbamoyl" as used herein refers to NH$_2$C(O)—.

The term "carbonyl($C_{1-8}$)-alkyl" as used herein refers to carbonyl substituted by ($C_{1-8}$)-alkyl as defined above.

The term "aryl" s used herein includes carbocyclic aromatic ring systems. Aryl is also intended to include the partially hydrogenated derivatives of the carbocyclic systems.

The term "heteroaryl" as used herein includes heterocyclic unsaturated ring systems containing one or more heteroatoms selected from nitrogen, oxygen and sulphur; such as e.g. furyl, thienyl, pyrrolyl and the like. Heteroaryl is also intended to include the partially hydrogenated derivatives of the heterocyclic systems enumerated below.

Examples of "aryl" and "heteroaryl" includes, but are not limited to phenyl, biphenyl, indene, fluorene, napthyl (1-naphthyl, 2-naphthyl), anthracene (1-anthracenyl, 2-anthracenyl, 3-anthracenyl), thiophene (2-thienyl, 3-thienyl), furyl (2-furyl, 3-furyl), indolyl, oxadiazolyl, isoxazolyl, thiadiazolyl, oxatriazolyl, thiatriazolyl, quinazolin, fluorenyl, xanthenyl, isoindanyl, benzhydryl, acridinyl, thiazolyl, pyrrolyl (1-pyrrolyl, 2-pyrrolyl, 3-pyrrolyl), pyrazolyl (1-pyrazolyl, 3-pyrazolyl, 4-pyrazolyl, 5-pyrazolyl), imidazolyl (1-imidazolyl, 2-imidazolyl, 4-imidazolyl, 5-imidazolyl), triazolyl (1,2,3-triazol-1-yl, 1,2,3-triazol-4-yl 1,2,3-triazol-5-yl, 1,2,4-triazol-3-yl, 1,2,4-triazol-5-yl), oxaxolyl (2-oxazolyl, 4-oxazolyl, 5-oxazolyl), isooxazolyl (isooxazo-3-yl, isooxazo-4yl, isooxaz-5-yl), isothiazolyl (isothiazo-3yl, isothiazo-4-yl, isothiaz-5-yl) thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl)), benzo[b]thiophenyl (benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), 2,3-dihydro-benzo[b]thiophenyl (2,3-dihydro-benzo[b]thiophen-2-yl, 2,3-dihydro-benzo[b]thiophen-3-yl, 2,3-dihydro-benzo[b]thiophen-4-yl, 2,3-dihydro-benzo[b]thiophen-5-yl, 2,3-dihydro-benzo[b]thiophen-6-yl, 2,3-dihydro-benzo[b]thiophen-7-yl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (2-benzoxaxolyl, 3-benzoxazolyl, 4-benzoxazolyl, 5-benzoxaolyl, 6-benzoxazolyl, 7-benzoxazolyl), benzothiazolyl (2-benzothiazolyl, 4-benzothiazolyl, 5-benzothiazolyl, 6-benzothiazolyl, 7-benzothiazolyl), carbazolyl (1-carbazolyl, 2-carbazolyl, 3-carboazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 11,11-dihydro-5H-dibenz[b,f]azepine-2-yl, 10,11-diydro-5H-dibenz[b,f]azepine-3-yl, 10,11-dihydro-5H-dibenz[b,f]azepine-4-yl, 10,11-dihydro-5H-dibenz[b,f]azepine-5-yl), benzo[1,3]dioxole (2-benzo[1,3]dioxole, 4-benzo[1,3]dioxole, 5-benzo[1,3]dioxole, 6-benzo[1,3]dioxole, 7-benzo[1,3]dioxole(, and tetrazolyl (5-tetrazolyl, N-tetrazolyl).

The present invention also relates to partly or fully saturated analogues of the ring systems mentioned above.

Certain of the above defined terms may occur more than once in the structural formulae, and upon such occurrence each term shall be defined independently of the other.

PHARMACEUTICAL COMPOSITIONS

In another aspect, the present invetnion includes within its scope pharmaceutical compositions comprising, as an active ingredient, at least one of the compounds of the general formula (I, Ia or Ib) or a pharmaceutically acceptable salt or prodrug or hydrate thereof together with a pharmaceutically acceptable carrier or diluent.

Optionally, a pharmaceutical composition of the present invention may comprise a compound of formula (I, Ia or Ib) combined with one or more compounds.

Pharmaceutical compositions containing a compound according to the present invention may be prepared by conventional techniques, e.g. as described in *Remington: The Science and Practise of Pharmacy*, 19$^{th}$ Ed., 1995. The comnposiitons may appear in conventional forms, for example capsules, tablets, aerosols, solutions, suspensions or topical applications.

Typical compositions include a compound of formula (I, Ia or Ib) or a pharmaceutically acceptable basic addition salt or prodrug or hydrate thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier, which may be in the form of a ampoule, capsule, sachet, paper, or other container. When the carrier serves as a diluent, it may be solid, semi-solid, or liquid material, which acts as a vehicle, excipient, or medium for the active compound. The active compound can be adsorbed on a granular solid container for example in a sachet. Some examples of suitable carriers are water, saolt solutions, alcohols, polyethylene glycols, polyhydroxyethoxylated castor oil, peanut oil, olive oil, gelatine, lactose, terra alba, sucrose, dextrin, magnesium carbonate, sugar, cyclodextrin, amylose, magnesium stearate, talc, gelatine, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethlcellulose and polyvinylpyrrolidone. Similarly, the carrier or diluent may include any sustained release material known in the art, such as glyceryl monostearate or glyceryl disterarate, alone or mixed with a wax. The formulations may also include wetting agents, emulsifying and suspending agents, preserving agents, sweetening agents or flavouring agents. The formulations of the present invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound of formula (I, Ia or Ib) to the appropriate or desired site of action, such as oral, nasal, pulmonary, buccal, subdermal, intradermal, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I, Ia or Ib dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. a syrup or elixir can be used in cases where a sweetened vehicle can be employed.

A typical tablet which may be prepared by conventional tabletting techniques may contain:

| Core: | |
|---|---|
| Active compound (as free compound or salt thereof) | 250 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Ad. |
| Coating: | |
| Hydroxypropylmethylcellulose (HPMC) approx. | 9 mg |
| *Mywacett 9–40 T approx. | 0.9 mg |

*Acylated monoglyceride used as plasticizer for film coating.

The compounds of the present invention may be administered to a mammal, especially a human, in need of such treatment, prevention, elimination, alleviation or amelioration of the various diseases as mentioned above, e.g. hyperglycemia, hypercholesterolemia, hypertension, hyperinsulinemia, hyperlioidemia or obesity, and especially diabetes. Such mammals also include animals, both domestic animals, e.g. household pets, and non-domestic animals such as wildlife.

The compounds of the present invention are effective over a wide dosage range. For example, in the treatment of adult humans, dosages from about 0.05 to about 1000 mg, preferably from about 0.1 to about 500 mg, per day may be used. A most preferably dosage is about 0.5 mg to about 250 mg per day. In chossing a regimen for patients it may frequently be necessary to begin with a higher dosage and when the condition is under control to reduce the dosage. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.05 to about 1000 mg of active ingredient together with a pharmaceutically acceptable carrier per unit dosage.

Usually, dosage forms suitable for oral, nasal, pulmonal or transdermal administration comprise from about 0.05 mg to about 1000 mg, preferably from about 0.5 mg to about 250 mg of the compounds of formula I, Ia or Ib admixed with a pharmaceutically acceptable carrier or diluent.

The present invention also encompasses prodrugs of a compound according to the invention which on administration undergo chemical conversion by metabolic processes being becoming active pharmacological substances. In general, such prodrugs will be functional derivatives of a compound according to the present invention which are readily convertible in vivo into a compound according to the present invention. Conventional procedures for the selection and preparation of suitable prodrug derivatives are described, for example, in "Design of Prodrugs", ed. H. Bundgaard, Elsevier, 1985. The ester derivatives of formula I, Ia or IB could be suitable prodrugs.

The present invention also encompasses active metabolites of a compound according to the invention.

In a further aspect of the present invention a compound according to the invention may be administered in combination with further pharmacologically active substances e.g. other antiobesity agents or appetite regulating agents.

Such agents may be selected from the group consisting of CART agonists, NPY antagonists, MC4 agonists, orexin antagonists, TNF agonists, CRF agonists, CRF BP antagonists, urocortin agonists, β3 agonists, MSH (melanocyte-stimulating hormone) agonists, MCH (melanocyte-concentrating hormone) antagonists, CCK agonists, serotonin re-uptake inhibitors, mixed serotonin and noradrenergic compounds, 5HT agonists, bombesin agonists, galanin antagonists, growth hormone, growth hormone releasing compounds, TRH agonists, uncoupling protein 2 or 3 modulators, GLP-1, leptin agonists, DA agonists (bromocriptin, doprexin), lipase/amylase inhibitors, PPAR modulators, RXR modulators or TR β agonists.

In a preferred embodiment of the present invention the antiobesity agent is leptin.

In another preferred embodiment the antiobesity agent is dexamphetamine or amphetamine.

In another preferred embodiment the antiobesity agent is dexfenfluramine.

In still another preferred embodiment the antiobesity agent is sibutramine.

In a further preferred embodiment the antiobesity agent is orlistat.

In another preferred embodiment the antiobesity agent is mazindol or phentermine.

In a further aspect of the present invention a compound according to the invention may be administered in combination with further pharmacologically active substances e.g. other lipid lowering agents.

A compound according to the present invention may also be administered in combination with an antidiabetic or other pharmacologically active material, including compounds for the treatment and/or prophylaxis of insulin resistance and diseases, wherein insulin resistance is the pathophysiological mechanism. Suitable antidiabetics comprise insulin, GLP-1 derivatives such as those disclosed in WO 98/08871 to Novo Nordisk A/S, which is incorporated herein by reference, as well as orally active hypoglycaemic agents.

The orally active hypoglycemic agents preferably comprise sulphonylureas, biguanides, oxadiazolidinediones, thiazolidinediones, α-glucosidase inhibitors, glucagon antagonists, GLP-1 agonists, potassium channel openers such as those disclosed in WO 97/26265 and WO 99/03861 to Novo Nordisk A/S, which are incorporated herein by reference, insulin sensitizers, hepatic enzyme inhibitors, glucose uptake modulators, compounds modifying the lipid metabolism, compounds lowering food intake, PPAR and RXR agonists and agents acting on the ATP-dependent potassium channel of the β-cells.

In a preferred embodiment of the present invention a compound according to the invention is administered in combination with insulin.

In a further preferred embodiment a compound according to the present invention is administered in combination with a sulphonylurea such as, e.g., tolbutamide, glibenclamide, glipizide and glicazide.

In another preferred embodiment a compound according to the present invention is administered in combination with a biguanidine such as, e.g., metformin.

In still another preferred embodiment a compound according to the present invention is administered in combination with a thiazolidinedione such as, e.g., troglitazone, ciglitazone, pioglitazone, rosiglitazone and the compounds disclosed in WO 97/41097 to Dr. Reddy's Research Foundation, especially 5-[[4-[(3,4-dihydro-3-methyl-4-oxo-2-quinazolinylmethoxy]phenyl]-methyl]-2,4-thiazolidinedione.

In a further preferred embodiment a compound according to the present invention is administered in combination with an agent acting on the ATP-dependent potassium channel of the β-cells such as, e.g,. tolbutamide, glibenclamide, glipizide, glicazide or repaglinide.

Furthermore, a compound according to the present invention may be administered in combination with an antihypertensive agent. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

Any novel feature or combination of features described herein is considered essential to this invention.

METHODS

In the Method and Examples the following terms are intended to have the following, general meaning:

| Abbreviations: | |
|---|---|
| DMF | N,N-dimethylformamide |
| THF | tetrahydrofuran |
| NMP | N-methylpyrrolidone |
| DMSO | dimethylsulphoxide |
| TEA | triethylamine |
| DMAP | 4-dimethylaminopyridine |
| Ph | phenyl |
| HOBt | N-hydroxybenzotriazole |
| EDAC | N-ethyl-N'-(3-dimethylaminopropyl)carbodiimide |
| Ts | Tosyl |
| Mp | Melting point |

The present invention also relates to methods of preparing the above-mentioned compounds.

The preparation of the compounds according to the present invention can be realized in many ways. These methods comprise:

1a) Reacting a compound of formula II with a compound of formula III in a solvent such as acetone, DMF, THF, NMP, DMSO, $CH_2Cl_2$ with a base such as NaOH, LiOH, TEA, DMAP, $K_2CO_3$, sodium hydride, potassium tert-butoxide, or sodium tert-butoxide to form a compound of formula IV.

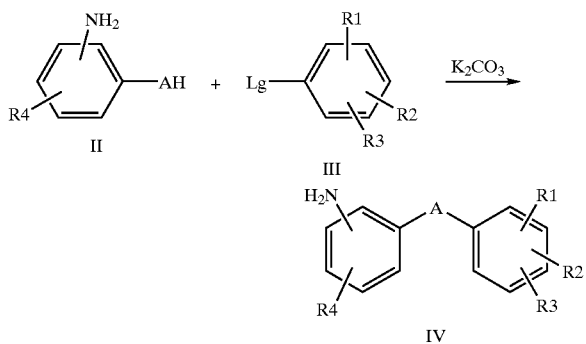

A is O or S. Lg is a leaving group such as F, Cl, Br, I, $NO_2$, $-OSO_2CH_3$ or -OTs.

R1, R2, R3 and R4 have the meanings set forth above. When R1, R2, R3, and R4 are labile groups e.g. acids or hydroxy they are protected as well known derivatives such as carboxylic esters, sulphonic esters, phosphoric esters, nitrile, amides, or cyclic anhydrides or cyclic amides or as e.g. ethers.

When A is >CO the compound is made by Friedel Craft acylation.

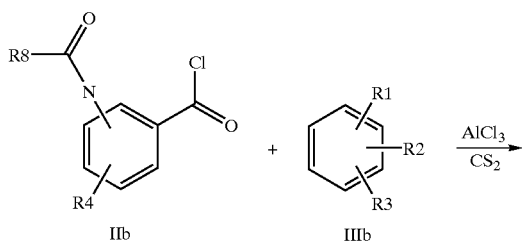

IIb and IIIb are reacted in a aprotic solvent such as $CS_2$ with a Friedel Craft catalyst such as $AlCl_3$, $FeCl_3$, $SnCl_4$ or $ZnCl_2$ to make IVb as described in J.Org.Chem 48(13) 2281–2285 (1983) or Justus Liebigs. Ann. Chem. 220, 250 (1993). Both references are incorporated herein by reference.

When A is >CR9R10 the reaction can be made by cross coupling or Grignard coupling.

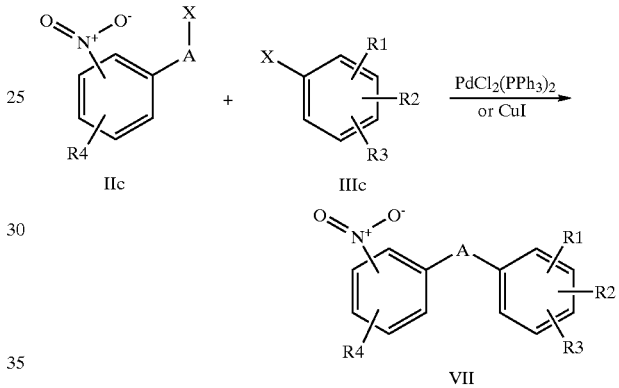

X is $B(OH)_2$, Cl, Br, I, ClMg-, BrMg-, or IMg- as described in synthetic Commun. 11, 513 (1981), Tetrahedron 54(12), 2953–2966 (1998), J.Chem.Soc.Chem.Com. 3, 305–306 (1995), J.Amer.Chem.Soc. 18(42), 10220–10227 (1996) or J.Chem.Soc.Per.Trans. 1(6) 719–730 (1993) all incorporated herein by reference.

If A in IIc is a >CO and X is H this reaction can be performed as a Friedel Craft coupling as described above, under Friedel Craft conditions described above.

R1, R2, R3, R4 and R8 have the meanings set forth above. When R1, R2, R3 and R4 are labile groups e.g. acids or hydroxy, they are protected as well known derivatives such as carboxylic esters, sulphonic esters, phosphoric esters, nitrile, amides, or cyclic anhydrides or cyclic amides or as e.g. ethers.

1b) Reacting a compound of formula V with a compound of formula VI in a solvent such as mentioned above with a base such as mentioned above to produce a compound of formula VII.

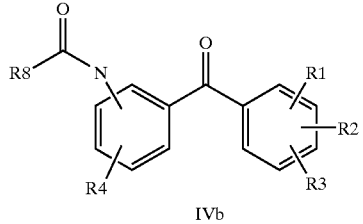

-continued

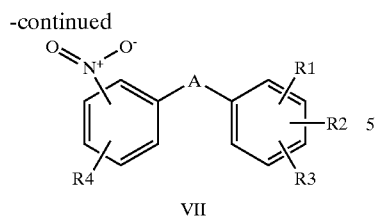

VII

A is O, S, or N and Lg, R1, R2, R3, and R4 have the meaning set forth above. Compounds of formula VII can be reduced by catalytic hydrogenation, $H_2$, Pd/C, to form compound IV.

2a) Reacting compound of formula IV with a compound of formula VIII in a solvent such as acetone, DMF, THF, $CH_2Cl_2$ or NMP with TEA, NaOH, LiOH, DMAP, $K_2CO_3$, sodium tert-butoxide or potassium tert-butoxide as base to produce a compound of formula IX.

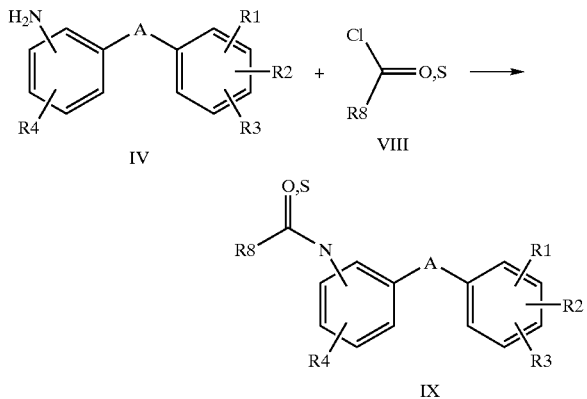

wherein A, R1, R2, R3, R4, and R8 have the meaning set forth above.

2b) A compound of formula IX can be synthesised from the $R8-CO_2H$ and the amine IV by coupling with HOBt, EDAC and TEA in a solvent such as DMF, $CH_2Cl_2$ or NMP to produce compounds of formula IX.

A compound of formula IV can be reacted with a compound of formula X like $Y-CH_2R8$, wherein Y is a leaving group such as Cl, Br, I, $-OSO_2CH_3$, or -OTs, to produce a compound of formula XI in a solvent such as acetone, DMF, DMSO, THF, NMP or $CH_2Cl_2$ with a base such as NaOH, LiOH, $K_2CO_3$, TEA, DMAP, sodium tert-butoxide, or potassium tert-butoxide.

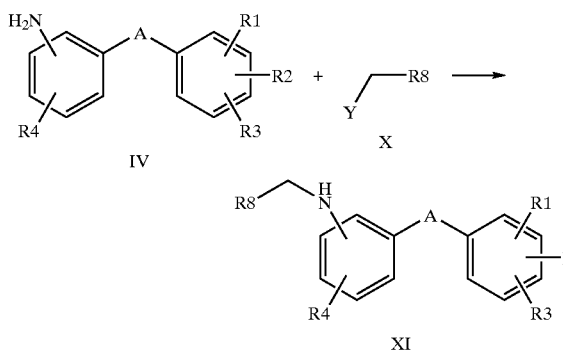

wherein A, R1, R2, R3, R4, and R8 have the meaning set forth above.

3a) Reacting a compound of formula (XIII), wherein A is O or S, and R2 and R3 have the meaning set forth above with a compound of the general formula (XII), wherein Su is a substrate and L is a linker to form a compound of the general formula (XIV):

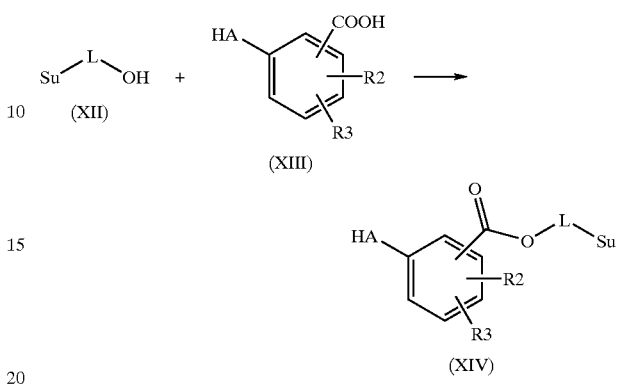

3b) Reacting a compound of formula (XIV) with a compound of formula (V) to form a compound of formula (XV), wherein A is O or S and Lg, L, Su, R2, R3, and R4 have the meaning set forth above or wherein A is C the AH group is CR6R7Br and Lg are $Sn(Me)_3$ or $B(OH)_2$ WO95/04277 (1995) or J.Am.Chem.Soc. 116, 11171–11172 (1994).

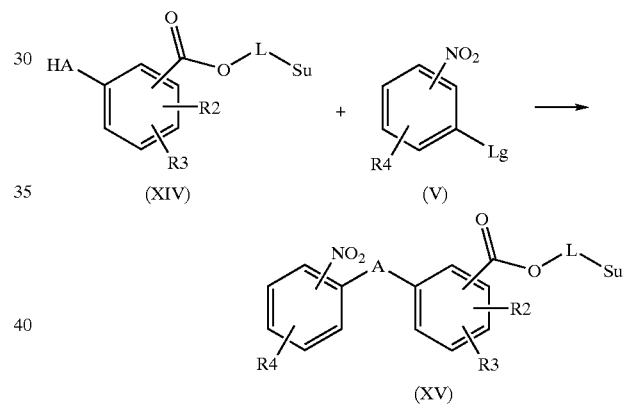

3c) Reducing a compound of formula (XV) to form a compound of formula (XVI) and reacting this compound with R8-COOH to produce a compound of formula (XVII):

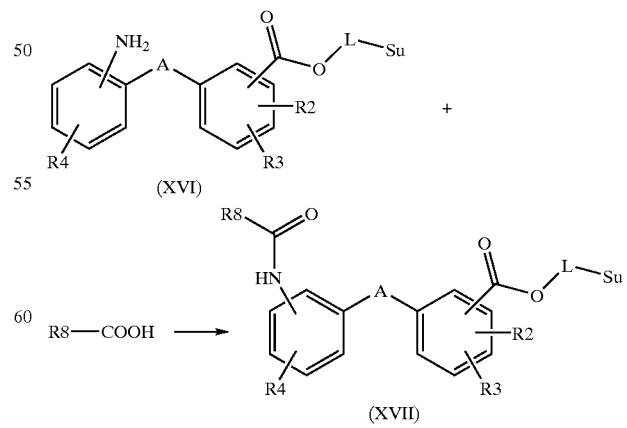

3d) Cleavage of a compound of formula (XVII) by e.g. treatment with a strong acid to form a compound of formula (I), wherein A is O, S or CR6R7, R1 is carboxylic acid, and R2, R3, R4, and R5 have the meaning set forth above.

The substrate Su may be any insoluble or partially insoluble material, to which compounds may be covalently attached. Substrates may be selected from the group consisting of any kind of organic or inorganic polymeric or oligomeric compound. Preferably the substrate may be selected from the groups consisting of polystyrene, polyethylene glycol (PEG), polyethylene glycol attached to polystyrene, polyacrylamides, polyamides, polysaccharides and silicates. Depending on the type of substrate chosen, different types of solvents or protecting groups may be used.

The linker L is a molecule with at least two reactive sites, which permit its covalent attachment to other molecules or to a substrate. Either the bond of the linker to the substrate or the bond of the linker to other molecules attached to it or the linker itself must be cleavable upon selective exposure to an activator such as a selected chemical activator or other specific conditions, e.g. by treatment with a strong acid or by exposure to electromagnetic radiation or by metal catalysis;

The starting materials employed in the synthesis of the compounds from formula II, III, V, VI and VIII are either known or may be prepared in conventional manner from commercially available materials, e.g according to the methods described in the examples.

Other compounds of the general formula I can be prepared by the above strategy. A variety of functional groups can be introduced in the compounds prepared as outlined above by methods well known to those skilled in the art.

The present invention is further illustrated by the following examples which, however, are not to be construed as limiting the scope of protection. The features disclosed in the foregoing description and in the following examples may, both separately and in any combination thereof, be material for realising the present invention in diverse forms thereof.

EXAMPLES

Example 1

4-[2-(3-Nitrobenzoylamino)phenoxy]phthalic acid (Compound 1)

To a suspension of Wang resin (1 g, 0.92 mmol, Bachem, loading : 0.92 mmol/g) in a mixture of methylene chloride (5 ml) and DMF (5 ml) were added 4-hydroxyphthalic acid (1.7 g, 9.3 mmol), diisopropyl carbodiimide (1.4 ml, 9.0 mmol) and 4-dimethylaminopyridine (66 mg, 0.54 mmol). The mixture was shaken for 20 hours and filtered. The resin was washed with DMF (4×10 ml), methylene chloride (4×10 ml), methanol (4×10 ml), and methylene chloride (4×10 ml). The resin was dried in vacuo. o-Fluoronitrobenzene (0.4 ml, 3.77 mmol) and 0.5 M potassium bis(trimethylsilyl)amide (1.2 ml, 0.6 mmol) were added to a suspension of the dried resin in DMF (4 ml). The mixture was shaken for 24 hours under a nitrogen atmosphere, filtered and the resin was washed with DMF (4×5 ml), methylene chloride (4×5 ml), DMF (4×5 ml), and N-methylpyrrolidone (4×5 ml). A solution of stannous chloride, dihydrate (0.9 g, 3.99 mmol) in N-methylpyrrolidone (4 ml) was added to the resin. The mixture was shaken for 24 hours, filtered and washed with N-methylpyrrolidone (4×5 ml), methylene chloride (4×5 ml), and methanol (4×5 ml). The resin was dried in vacuo to give approx. 244 mg material.

To a suspension of this resin (20 mg, 0.0184 mmol) in a mixture of DMF (1 ml) and methylene chloride (1 ml) were added 3-nitrobenzoic acid (30 mg, 0.180 mmol) and diisopropyl carbodiimide (12 µl, 0.077 mmol). The mixture was shaken for 24 hours, filtered and the resin washed with DMF (4×4 ml), THF (4×4 ml), and methylene chloride (4×4 ml). The resin was shaken with methylene chloride:trifluoroacetic acid (1:1) (2 ml) for 20 minutes. The mixture was filtered and the resin washed with tetrachloro methane (4 ml) and the collected filtrates were evaporated to dryness in vacuo to give 4-[2-(3-nitrobenzoylamino)-phenoxy]phthalic acid (5.5 mg, yield: 70%) as light crystals.

$^1$H-NMR (DMSO-$d_6$) in ppm: γ 10.3 (s, 1H), 8.58 (m, 1H), 8.38 (m, 1H), 8.18 (d, 1H), 7.6–7.8 (m, 3H), 7.3–7.4 (m, 2H), 7.18 (d.d., 1H), 7.1 (m, 1H), 7.07 (d.d., 1H). LC-MS: m/e 223 (MH$^+$), 205 (MH$^+$-H$_2$O).

In a similar way the following compounds were prepared:

4-{2-[2-(2-Carboxyphenyl)acetylamino]phenoxy}phthalic acid (Compound 2) was prepared according to the method described above using homophthalic acid instead of 3-nitrobenzoic acid. LC-MS: m/e 436 (MH$^+$)

4-[2-(2-Bromobenzoylamino)phenoxy]phthalic acid (Compound 3) was prepared according to the method described above using 2-bromobenzoic acid instead of 3-nitrobenzoic acid. LC-MS: m/e 456/458 (MH$^+$), 438/440 (MH$^+$-H$_2$O).

4-[2-(2-Chlorobenzoylamino)phenoxy]phthalic acid (Compound 4) was prepared according to the method described above using 2-chlorobenzoic acid instead of 3-nitrobenzoic acid. LC-MS: m/e 412 (MH$^+$), 394 (MH$^+$-H$_2$O).

4-[2-(4-Chlorobenzoylamino)phenoxy]phthalic acid (Compound 5) was prepared according to the method described above using 4-chlorobenzoic acid instead of 3-nitrobenzoic acid. LC-MS: m/e 412 (MH$^+$), 394 (MH$^+$-H$_2$O).

4-[2-(3-Methoxybenzoylamino)phenoxy]phthalic acid (Compound 6) was prepared according to the method described above using 3-methoxybenzoic acid instead of 3-nitrobenzoic acid. LC-MS: m/e 408 (MH$^+$), 390 (MH$^+$-H$_2$O).

4-[2-(2-Carboxybenzoylamino)phenoxy]phthalic acid (Compound 7) was prepared according to the method described above using phthalic acid instead of 3-nitrobenzoic acid. LC-MS: m/e 422 (MH$^+$).

4-[2-(2-Methoxybenzoylamino)phenoxy]phthalic acid (Compound 8) was prepared according to the method described above using 2-methoxybenzoic acid instead of 3-nitrobenzoic acid. LC-MS: m/e 408 (MH$^+$), 390 (MH$^+$-H$_2$O).

4-[2-(4-Acetylaminobenzoylamino)phenoxy]phthalic acid (Compound 9) was prepared according to the method described above using 4-acetamidobenzoic acid instead of 3-nitrobenzoic acid. LC-MS: m/e 435 (MH$^+$), 417 (MH$^+$-H$_2$O).

4-[2-(4-Methoxybenzoylamino)phenoxy]phthalic acid (Compound 10) was prepared according to the method described above using 4-methoxybenzoic acid instead of 3-nitrobenzoic acid. LC-MS: m/e 408 (MH$^+$), 390 (MH$^+$-H$_2$O).

4-[2-(3,4,5-Trimethoxybenzoylamino)phenoxy]phthalic acid (Compound 11) was prepared according to the method described above using 3,4,5-trimethoxybenzoic acid instead of 3-nitrobenzoic acid. LC-MS: m/e 468 (MH$^+$), 450 (MH$^+$-H$_2$O).

4-{2-[(Naphthalene-1-carbonyl)amino]phenoxy}phthalic acid (Compound 12) was prepared according to the method described above using 1-naphthoic acid instead of 3-nitrobenzoic acid. LC-MS: m/e 428 (MH$^+$), 410 (MH$^+$-H$_2$O).

4-{2-[(Naphthalene-2-carbonyl)amino]phenoxy}phthalic acid (Compound 13) was prepared according to the method described above using 2-naphthoic acid instead of 3-nitrobenzoic acid. LC-MS: m/e 428 ($MH^+$), 410 ($MH^+$-$H_2O$).

4-[2-(2-Acetylbenzoylamino)phenoxy]phthalic acid (Compound 14) was prepared according to the method described above using 2-acetyl benzoic acid instead of 3-nitrobenzoic acid. LC-MS: m/e 420 ($MH^+$).

4-[2-(4-Ethoxybenzoylamino)phenoxy]phthalic acid (Compound 15) was prepared according to the method described above using 4-ethoxybenzoic acid instead of 3-nitrobenzoic acid. LC-MS: m/e 422 ($MH^+$), 404 ($MH^+$-$H_2O$).

4-{2-[(Benzo[1,3]dioxole-5-carbonyl)amino]phenoxy}phthalic acid (Compound 16) was prepared according to the method described above using piperonylic acid instead of 3-nitrobenzoic acid. LC-MS: m/e 422 ($MH^+$), 404 ($MH^+$-$H_2O$).

4-[2-(2,5-Dichlorobenzoylamino)phenoxy]phthalic acid (Compound 17) was prepared according to the method described above using 2,5-dichlorobenzoic acid instead of 3-nitrobenzoic acid. LC-MS: m/e 446 ($MH^+$), 428 ($MH^+$-$H_2O$).

4-[2-(4-Bromobenzoylamino)phenoxy]phthalic acid (Compound 18) was prepared according to the method described above using 4-bromobenzoic acid instead of 3-nitrobenzoic acid. LC-MS: m/e 456/458 ($MH^+$), 438/440 ($MH^+$-$H_2O$).

4-[2-(3-Dimethylaminobenzoylamino)phenoxy]phthalic acid (Compound 19) was prepared according to the method described above using 3-dimethylaminobenzoic acid instead of 3-nitrobenzoic acid. LC-MS: m/e 421 ($MH^+$), 403 ($MH^+$-$H_2O$).

4-[2-(4-Trifluoromethoxybenzoylamino)phenoxy]phthalic acid (Compound 20) was prepared according to the method described above using 4-trifluoromethoxybenzoic acid instead of 3-nitrobenzoic acid. LC-MS: m/e 462 ($MH^+$), 444 ($MH^+$-$H_2O$).

4-[2-(3,5-Dimethoxybenzoylamino)phenoxy]phthalic acid (Compound 21) was prepared according to the method described above using 3,5-dimethoxybenzoic acid instead of 3-nitrobenzoic acid. LC-MS: m/e 438 ($MH^+$), 420 ($MH^+$-$H_2O$).

4-[2-(5-Chloro-2-methoxybenzoylamino)phenoxy]phthalic acid (Compound 22) was prepared according to the method described above using 5-chloro-2-methoxybenzoic acid instead of 3-nitrobenzoic acid. LC-MS: m/e 422 ($MH^+$), 424 ($MH^+$-$H_2O$).

4-[2-(3,4-Difluorobenzoylamino)phenoxy]phthalic acid (Compound 23) was prepared according to the method described above using 3,4-difluorobenzoic acid instead of 3-nitrobenzoic acid. LC-MS: m/e 414 ($MH^+$), 396 ($MH^+$-$H_2O$).

4-[2-(2-Iodobenzoylamino)phenoxy]phthalic acid (Compound 24) was prepared according to the method described above using 2-iodobenzoic acid instead of 3-nitrobenzoic acid. LC-MS: m/e 504 ($MH^+$), 486 ($MH^+$-$H_2O$).

4-[2-(2,4-Dimethoxybenzoylamino)phenoxy]phthalic acid (Compound 25) was prepared according to the method described above using 2,5-dimethoxybenzoic acid instead of 3-nitrobenzoic acid. LC-MS: m/e 438 ($MH^+$), 420 ($MH^+$-$H_2O$).

4-[2-(3-Iodobenzoylamino)phenoxy]phthalic acid (Compound 26) was prepared according to the method described above using 3-iodobenzoic acid instead of 3-nitrobenzoic acid. LC-MS: m/e 504 ($MH^+$), 486 ($MH^+$-$H_2O$).

4-[2-(3,5-Dimethylbenzoylamino)phenoxy]phthalic acid (Compound 27) was prepared according to the method described above using 3,5-dimethylbenzoic acid instead of 3-nitrobenzoic acid.

4-{2-[2-(4-Chlorobenzoyl)benzoylamino]phenoxy}phthalic acid (Compound 28) was prepared according to the method described above using 4-(chlorobenzoyl)benzoic acid instead of 3-nitrobenzoic acid. LC-MS: m/e 516 ($MH^+$), 498 ($MH^+$-$H_2O$).

4-{2-[2-(4-Fluorobenzoyl)benzoylamino]phenoxy}phthalic acid (Compound 29) was prepared according to the method described above using 4-(fluorobenzoyl)benzoic acid instead of 3-nitrobenzoic acid. LC-MS: m/e 500 ($MH^+$), 482 ($MH^+$-$H_2O$).

4-[2-(2-Chloro-4-fluorobenzoylamino)phenoxy]phthalic acid (Compound 30) was prepared according to the method described above using 2-chloro-4-fluorobenzoic acid instead of 3-nitrobenzoic acid. LC-MS: m/e 430 ($MH^+$), 412 ($MH^+$-$H_2O$).

4-{2-[(2,3-Dihydrobenzofuran-7-carbonyl)amino]phenoxy}phthalic acid (Compound 31) was prepared according to the method described above using 7-(2,3-dihydrobenzofuranyl)-carboxylic acid instead of 3-nitrobenzoic acid. LC-MS: m/e 420 ($MH^+$), 402 ($MH^+$-$H_2O$).

4-[2-(4-tert-Butylbenzoylamino)phenoxy]phthalic acid (Compound 32) was prepared according to the method described above using 4-tert-butylbenzoic acid instead of 3-nitrobenzoic acid. LC-MS: m/e 434 ($MH^+$), 416 ($MH^+$-$H_2O$).

4-[2-(3,4-Dichlorobenzoylamino)phenoxy]phthalic acid (Compound 33) was prepared according to the method described above using 3,4-dichlorobenzoic acid instead of 3-nitrobenzoic acid. LC-MS: m/e 466 ($MH^+$), 428 ($MH^+$-$H_2O$).

4-[2-(2-Fluoro-5-trifluoromethylbenzoylamino)phenoxy]phthalic acid (Compound 34) was prepared according to the method described above using 2-fluoro-5-trifluorobenzoic acid instead of 3-nitrobenzoic acid. LC-MS: m/e 464 ($MH^+$), 446 ($MH^+$-$H_2O$).

4-[2-(2-Fluorobenzoylamino)phenoxy]phthalic acid (Compound 35) was prepared according to the method described above using 2-fluorobenzoic acid instead of 3-nitrobenzoic acid. LC-MS: m/e 396 ($MH^+$), 378 ($MH^+$-$H_2O$).

4-[2-(3-Benzoyl-benzoylamino)phenoxy]phthalic acid (Compound 36) was prepared according to the method described above using benzophenone-3-carboxylic acid instead of 3-nitrobenzoic acid. LC-MS: m/e 482 ($MH^+$), 464 ($MH^+$-$H_2O$).

4-{2-[2-(4-Methylbenzoyl)benzoylamino]phenoxy}phthalic acid (Compound 37) was prepared according to the method described above using 2-(4-toloyl)benzoic acid instead of 3-benzoic acid. LC-MS: m/e 496 ($MH^+$), 478 ($MH^+$-$H_2O$).

4-[2-(3-Acetylbenzoylamino)phenoxy]phthalic acid (Compound 38) was prepared according to the method described above using 3-acetylbenzoic acid instead of 3-nitrobenzoic acid. LC-MS: m/e 420 ($MH^+$), 402 ($MH^+$-$H_2O$).

4-[2-(2,3-Dimethoxybenzoylamino)phenoxy]phthalic acid (Compound 39) was prepared according to the method described above using 2,3-dimethoxybenzoic acid instead of 3-nitrobenzoic acid. LC-MS: m/e 438 ($MH^+$), 420 ($MH^+$-$H_2O$).

4-[2-(2-Benzylbenzoylamino)phenoxy]phthalic acid (Compound 40) was prepared according to the method described above using α-phenyl-o-toluic acid instead of 3-nitrobenzoic acid. LC-MS: m/e 468 (MH$^+$), 450 (MH$^+$-H$_2$O).

4-{2-[(5-Methoxy-2-methyl-2,3-dihydrobenzofuran-7-carbonyl)amino]phenoxy}phthalic acid (Compound 41) was prepared according to the method described above using 2-methyl-5-methoxy-2,3-dihydrobenzo(b)furan-7-carboxylic acid instead of 3-nitrobenzoic acid. LC-MS: m/e 464 (MH$^+$), 446 (MH$^+$-H$_2$O).

4-[2-(4-Methyl-benzoylamino)phenoxy]phthalic acid (Compound 42) was prepared according to the method described above using p-toluic instead of 3-nitrobenzoic acid. LC-MS: m/e 392 (MH$^+$), 374 (MH$^+$-H$_2$O).

4-{2-[(4-Chloro-2-methyl-2,3-dihydrobenzofuran-7-carbonyl)amino]phenoxy}phthalic acid (Compound 43) was prepared according to the method described above using 2-methyl-4-chloro-2,3-dihydrobenzo(b)furan-7-carboxylic acid instead of 3-nitrobenzoic acid. LC-MS: m/e 468 (MH$^+$), 450 (MH$^+$-H$_2$O).

4-{2-[(2-Methylbenzofuran-7-carbonyl)amino]phenoxy}phthalic acid (Compound 44) was prepared according to the method described above using 2-methylbenzo(b)furan-7-carboxylic acid instead of 3-nitrobenzoic acid. LC-MS: m/e 432 (MH$^+$), 414 (MH$^+$-H$_2$O).

4-[2-(4-Iodobenzoylamino)phenoxy]phthalic acid (Compound 45) was prepared according to the method described above using 4-iodobenzoic acid instead of 3-nitrobenzoic acid. LC-MS: m/e 504 (MH$^+$), 486 (MH$^+$-H$_2$O).

4-[2-(5-Bromo-2-methoxybenzoylamino)phenoxy]phthalic acid (Compound 46) was prepared according to the method described above using 2-methoxy-5-bromobenzoic acid instead of 3-nitrobenzoic acid. LC-MS: m/e 486/488 (MH$^+$), 468/470 (MH$^+$-H$_2$O).

4-[2-(2-Benzyloxy-5-chlorobenzoylamino)phenoxy]phthalic acid (Compound 47) was prepared according to the method described above using 2-benzyloxy-5-chlorobenzoic acid instead of 3-nitrobenzoic acid. LC-MS: m/e 518 (MH$^+$), 500 (MH$^+$-H$_2$O).

4-[2-(3-Bromobenzoylamino)phenoxy]phthalic acid (Compound 48) was prepared according to the method described above using 3-bromobenzoic acid instead of 3-nitrobenzoic acid. LC-MS: m/e 456/458 (MH$^+$), 438/440 (MH$^+$-H$_2$O).

4-[2-(3-Chlorobenzoylamino)phenoxy]phthalic acid (Compound 49) was prepared according to the method describe above using 3-chlorobenzoic acid instead of 3-nitrobenzoic acid. LC-MS: m/e 412 (MH$^+$), 394 (MH$^+$-H$_2$O).

4-[2-(3,4,5-Tribromobenzoylamino)phenoxy]phthalic acid (Compound 50) was prepared according to the method described above using 3,4,5-tribromobenzoic acid instead of 3-nitrobenzoic acid. LC-MS: m/e 612, 614, 616, 618 (1:3:3:1) (MH$^+$), 594, 596, 598, 600 (1:3:3:1) (MH$^+$-H$_2$O).

4-[2-(3,5-Dibromobenzoylamino)phenoxy]phthalic acid (Compound 51) was prepared according to the method described above using 3,5-dibromobenzoic acid instead of 3-nitrobenzoic acid. LC-MS: m/e 534, 536, 538 (1:2:1) (MH$^+$), 516, 518, 520 (1:2:1) (MH$^+$-H$_2$O).

4-[2-(4-Methanesulphonylbenzoylamino)phenoxy]phthalic acid (Compound 52) was prepared according to the method described above using 4-methylsulphonylbenzoic acid instead of 3-nitrobenzoic acid. LC-MS: m/e 456 (MH$^+$), 438 (MH$^+$-H$_2$O).

4-[2-(3,4-Dimethylbenzoylamino)phenoxy]phthalic acid (Compound 53) was prepared according to the method described above using 3,4-dimethylbenzoic acid instead of 3-nitrobenzoic acid. LC-MS: m/e 406 (MH$^+$), 388 (MH$^+$-H$_2$O).

4-[2-(3,5-Dichlorobenzoylamino)phenoxy]phthalic acid (Compound 54) was prepared according to the method described above using 3,5-dichlorobenzoic acid instead of 3-nitrobenzoic acid. LC-MS: m/e 446 (MH$^+$), 428 (MH$^+$-H$_2$O).

4-[2-(2-Bromo-4-fluorobenzoylamino)phenoxy]phthalic acid (Compound 55) was prepared according to the method described above using 2-bromo-4-fluorobenzoic acid instead of 3-nitrobenzoic acid. LC-MS: m/e 474, 476 (MH$^+$), 456, 458 (MH$^+$-H$_2$O).

4-[2-(2-Chloro-6-fluorobenzoylamino)phenoxy]phthalic acid (Compound 56) was prepared according to the method described above using 2-chloro-6-fluorobenzoic acid instead of 3-nitrobenzoic acid. LC-MS: m/e 430 (MH$^+$), 412 (MH$^+$-H$_2$O).

4-[2-(2,6-Difluoro-benzoylamino)phenoxy]phthalic acid (Compound 57) was prepared according to the method described above using 2,6-difluorobenzoic acid instead of 3-nitrobenzoic acid. LC-MS: m/e 414 (MH$^+$), 396 (MH$^+$-H$_2$O).

4-[2-(4-Isopropylbenzoylamino)phenoxy]phthalic acid (Compound 58) was prepared according to the method described above using 4-isopropylbenzoic acid instead of 3-nitrobenzoic acid. LC-MS: m/e 420 (MH$^+$), 402 (MH$^+$-H$_2$O).

4-[2-(4-n-Pentylbenzoylamino)phenoxy]phthalic acid (Compound 59) was prepared according to the method described above using 4-n-pentylbenzoic acid instead of 3-nitrobenzoic acid. LC-MS: m/e 448 (MH$^+$), 430 (MH$^+$-H$_2$O).

4-[2-(4-n-Heptylbenzoylamino)phenoxy]phthalic acid (Compound 60) was prepared according to the method described above using 4-n-heptylbenzoic acid instead of 3-nitrobenzoic acid. LC-MS: m/e 476 (MH$^+$), 458 (MH$^+$-H$_2$O).

4-[2-(4-Trifluoromethylbenzoylamino)phenoxy]phthalic acid (Compound 61) was prepared according to the methods described above using 4-trifluoromethylbenzoic acid instead of 3-nitrobenzoic acid. LC-MS: m/e 446 (MH$^+$), 428 (MH$^+$-H$_2$O).

4-[2-(5-Bromo-2-chlorobenzoylamino)phenoxy]phthalic acid (Compound 62) was prepared according to the method described above using 2-bromo-2-chlorobenzoic acid instead of 3-nitrobenzoic acid. LC-MS: m/e 490, 492 (MH$^+$), 472, 474 (MH$^+$-H$_2$O).

4-[2-(2,3-Difluorobenzoylamino)phenoxy]phthalic acid (Compound 63) was prepared according to the method described above using 2,3-difluorobenzoic acid instead of 3-nitrobenzoic acid. LC-MS: m/e 414 (MH$^+$), 396 (MH$^+$-H$_2$O).

4-[2-(4-Bromo-2-chlorobenzoylamino)phenoxy]phthalic acid (Compound 64) was prepared according to the method described above using 4-bromo-2-chlorobenzoic acid instead of 3-nitrobenzoic acid. LC-MS: m/e 490, 492 (MH$^+$), 472, 474 (MH$^+$-H$_2$O).

4-[2-(2-Chloro-5-iodobenzoylamino)phenoxy]phthalic acid (Compound 65) was prepared according to the method described above using 2-chloro-5-iodobenzoic acid instead of 3-nitrobenzoic acid. LC-MS: m/e 538 (MH$^+$), 520 (MH$^+$-H$_2$O).

4-[2-(4-Methylthiobenzoylamino)phenoxy]phthalic acid (Compound 66) was prepared according to the method described above using 4-methylthiobenzoic acid instead of 3-nitrobenzoic acid. LC-MS: m/e 424 (MH$^+$), 406 (MH$^+$-H$_2$O).

4-[2-(2,4-Difluorobenzoylamino)phenoxy]phthalic acid (Compound 67) was prepared according to the method described above using 2,4-difluorobenzoic acid instead of 3-nitrobenzoic acid. LC-MS: m/e 414 (MH$^+$), 396 (MH$^+$-H$_2$O).

4-[2-(2,5-Difluorobenzoylamino)phenoxy]phthalic acid (Compound 68) was prepared according to the method described above using 2,5-difluorobenzoic acid instead of 3-nitrobenzoic acid. LC-MS: m/e 414 (MH$^+$), 396 (MH$^+$-H$_2$O).

4-[2-(4-Fluorobenzoylamino)phenoxy]phthalic acid (Compound 69) was prepared according to the method described above using 4-fluorobenzoic acid instead of 3-nitrobenzoic acid. LC-MS: m/e 396 (MH$^+$), 378 (MH$^+$-H$_2$O).

4-(2-Benzoylaminophenoxy)phthalic acid (Compound 70) was prepared according to the method described above using benzoic acid instead of 3-nitrobenzoic acid. LC-MS: m/e 378 (MH$^+$), 360 (MH$^+$-H$_2$O).

4-[2-(2,4-Dichlorobenzoylamino)phenoxy]phthalic acid (Compound 71) was prepared according to the method described above using 2,4-dichlorobenzoic acid instead of 3-nitrobenzoic acid. LC-MS: m/e 446 (MH$^+$), 428 (MH$^+$-H$_2$O).

4-[2-(3-Methylbenzoylamino)phenoxy]phthalic acid (Compound 72) was prepared according to the method described above using 3-methylbenzoic acid instead of 3-nitrobenzoic acid. LC-MS: m/e 392 (MH$^+$), 374 (MH$^+$-H$_2$O).

4-[2-(3-Cyanobenzoylamino)phenoxy]phthalic acid (Compound 73) was prepared according to the method described above using 3-cyanobenzoic acid instead of 3-nitrobenzoic acid. LC-MS: m/e 403 (MH$^+$), 385 (MH$^+$-H$_2$O).

4-[4-Amino-2-(3-nitrobenzoylamino)phenoxy]phthalic acid (Compound 74) was prepared according the method described above using N-(tert-butoxycarbonyl)-4-fluoro-3-nitroaniline instead of o-fluoronitrobenzene. LC-MS: m/e 438 (MH$^+$), 420 (MH$^+$-H$_2$O).
$^1$H-NMR (D$_6$-DMSO) in ppm: δ 10.1 (1H,s), 8.5 (1H,s), 8.3 (1H,d.d.), 8.1 (1H,d), 7.70 (1H,t), 7.67 (1H,d), 6.97 (3H,d.d.), 6.91 (1H,d), 6.6 (1H,d.d.).

4-[2-(2-Thiophen-2-yl-acetylamino)phenoxy]phthalic acid (Compound 75) was prepared according the method described above using 2-thienylacetic acid instead of 3-nitrobenzoic acid.
$^1$H-NMR (D$_6$-DMSO) in ppm: δ 9.67 (1H,s), 7.98 (1H,d), 7.73 (1H,d), 7.32 (1H,d), 7.23 (2H,p), 7.09 (2H,m), 7.03 (1H,d.d.), 6.91 (1H,d), 6.85 (1H,d).

4-{2-[(Furan-2-carbonyl)amino]phenoxy}phthalic acid (Compound 76) was prepared according the method described above using 2-furoic acid instead of 3-nitrobenzoic acid.
$^1$H-NMR (D$_6$-DMSO) in ppm: δ 9.5 (1H,s), 7.85 (1H,s), 7.7–7.8 (2H,m), 7.25–7.32 (2H,m), 7.22 (1H,d), 7.1–7.15 (3H,m), 6.65 (1H,d).

4-[2,4-Bis-(3-nitrobenzoylamino)phenoxy]phthalic acid (Compound 77) was prepared according the method described above using 1-fluoro-2,4-dinitrobenzene instead of o-fluoronitrobenzene. LC-MS: m/e 609 (M+Na), 604 (M+NH$_4^+$), 569 (MH$^+$-H$_2$O).
$^1$H-NMR (D$_6$-DMSO) in ppm: δ 10.8 (1H,s); 10.5 (1H,s); 8.83 (1H,t); 8.56 (1H,t); 8.36–8.49 (3H,m); 8.24 (1H,d); 8.18 (1H,d); 7.87 (1H,t); 7.72–7.8 (3H,m); 7.24 (1H,d), 7.09 (2H,d.d.).

4-[2-(3-Nitrobenzoylamino)-4-trifluoromethylphenoxy] phthalic acid (Compound 78) was prepared according the method described above using 1-fluoro-2-nitro-4-trifluoromethylbenzene instead of o-fluoronitrobenzene. LC-MS: m/e 513 (M+Na), 491 (M+NH$_4^+$), 473 (MH$^+$-H$_2$O).
$^1$H-NMR (D$_6$-DMSO) in ppm: δ 10.58 (1H,s); 8.64 (1H,s); 8.43 (1H,d.d.); 8.25 (1H,d); 8.17 (1H,s); 7.74–7.84 (2H,m); 7.68 (1H,d.d.), 7.31 (1H,d); 7.19–7.27 (2H,m).

4-[5-Methyl-2-(3-nitrobenzoylamino)phenoxy]phthalic acid (Compound 79) was prepared according the method described above using 2-fluoro-1-nitro-4-methylbenzene instead of o-fluoronitrobenzene. LC-MS: m/e 459 (M+Na), 419 (MH$^+$-H$_2$O).
$^1$H-NMR (D$_6$-DMSO) in ppm: δ 10.26 (1H,s); 8.55 (1H,s); 8.38 (1H,d.d.); 8.17 (1H,d); 7.48 (1H,t); 7.7 (1H,d); 7.58 (1H,d); 7.17 (1H,d.d.); 7.05 . 7.1 (2H,m); 7.0 (1H,s); 2.8 (3H,s).

4-[4-Fluoro-2-(3-nitrobenzoylamino)phenoxy]phthalic acid (Compound 80) was prepared according the method described above using 1,4-difluoro-2-nitrobenzene instead of o-fluoronitrobenzene. LC-MS: m/e 463 (M+Na), 441 (MH$^+$), 423 (MH$^+$-H$_2$O).
$^1$H-NMR (D$_6$-DMSO) in ppm: δ 10.44 (1H,s); 8.54 (1H,t); 8.39 (1H,d.d.); 8.15 (1H,d); 7.76 (1H,t); 7.65–7.73 (2H,m); 7.27 (1H,d.d.); 7.19 (1H,d.d.); 7.05–7.1 (2H,m).

4-[4-Methyl-2-(3-nitrobenzoylamino)phenoxy]phthalic acid (Compound 81) was prepared according the method described above using 1-fluoro-2-nitro-4-methylbenzene instead of o-fluoronitrobenzene. LC-MS: m/e 459 (M+Na), 437 (MH$^+$), 419 (MH$^+$-H$_2$O).
$^1$H-NMR (D$_6$-DMSO) in ppm: δ 10.28 (1H,s); 8.55 (1H,s); 8.38 (1H,d); 8.16 (1H,d); 7.75 (1H,t); 7.7 (1H,d); 7.5 (1H,s); 7.17 (1H,d); 7.0–7.1 (3H,m); 2.8 (3H,s).

4-[5-Bromo-4-fluoro-2-(3-nitrobenzoylamino)phenoxy] phthalic acid (Compound 82) was prepared according the method described above using 5-bromo-1,4-difluoro-2-nitrobenzene instead of o-fluoronitrobenzene. LC-MS: m/e 519/521 (MH$^+$), 501/503 (MH$^+$-H$_2$O).

4-[4-Methanesulfonyl-2-(3-nitrobenzoylamino)phenoxy] phthalic acid (Compound 83) was prepared according the method described above using 4-fluoro-3-nitrophenyl methyl sulfone instead of o-fluoronitrobenzene.

4-[4,5-Dichloro-2-(3-nitrobenzoylamino)phenoxy]phthalic acid (Compound 84) was prepared according the method described above using 1,2-dichloro-4-fluoro-5-nitrobenzene instead of o-fluoronitrobenzene.
$^1$H-NMR (D$_6$-DMSO) in ppm: δ 10.53 (1H,s); 8.55 (1H,s); 8.4 (1H,d.d.); 8.16 (1H,d); 8.06 (1H,s); 7.7 (1H,d); 7.74 (1H,d); 7.52 (1H,s); 7.12–7.20 (2H,m).

4-[4-Cyano-2-(3-nitrobenzoylamino)phenoxy]phthalic acid (Compound 85) was prepared according the method described above using 4-fluoro-3-nitrobenzonitrile instead of o-fluoronitrobenzene.
$^1$H-NMR (D$_6$-DMSO) in ppm: δ 10.58 (1H,s); 8.6 (1H,t); 8.41 (1H,d.d.); 8.18–8.24 (2H,m); 7.78 (2H,d); 7.75 (1H, d.d.); 7.28 (1H,d), 7.2–7.25 (2H,m).

4-[5-Methyl-2,4-bis-(3-nitrobenzoylamino)phenoxy] phthalic acid (Compound 86) was prepared according the method described above using 5-fluoro-2,4-dinitrotoluen instead of o-fluoronitrobenzene.
$^1$H-NMR (D$_6$-DMSO) in ppm: δ 10.35 (1H,s); 8.75 (1H,t); 8.46 (1H,s); 8.42 (1H,d); 7.37 (1H,d); 8.33 (1H,d); 8.1 (1H,d); 7.82 (1H,t); 7.66–7.2 (3H,m); 7.08–7.13 (3H,m).

4-[4-Benzoylamino-2-(3-nitrobenzoylamino)phenoxy] phthalic acid (Compound 87) was prepared according the method described above using N-(4-fluoro-3-nitrophenyl)-benzylamide instead of o-fluoronitrobenzene.

¹H-NMR (D₆-DMSO) in ppm: δ 10.42 (1H,s); 10.38 (1H,s); 8.5 (1H,s); 8.37 (1H,d.d.); 8.18 (1H,d); 8.15 (1H,d); 7.96 (2H,d); 7.73 (2H,t); 7.67 (1H,d); 7.5–7.62 (3H,m); 7.2 (1H,d); 7.02–7.1 (2H,m).

4-[4-Bromo-2-(3-nitrobenzoylamino)phenoxy]phthalic acid (Compound 88) was prepared according the method described above using 4-bromo-2-fluoro-1-nitrobenzen instead of o-fluoronitrobenzene.

¹H-NMR (D₆-DMSO) in ppm: δ 10.46 (1H,s); 8.56 (1H,s); 8.4 (1H,d.d.); 8.17 (1H,d); 7.96 (1H,d); 7.76 (1H,t); 7.72 (1H,d); 7.51 (1H,d.d.); 7.1–7.18 (3H,m).

4-[5-Fluoro-2-(3-nitrobenzoylamino)phenoxy]phthalic acid (Compound 89) was prepared according the method described above using 2,4-difluoro-1-nitrobenzen instead of o-fluoronitrobenzene. LC-MS: m/e 463 (M+Na), 441 (MH⁺), 423 (MH⁺-H₂O).

¹H-NMR (D₆-DMSO) in ppm: 10.33 (1H,s); 8.48 (1H,s); 8.34 (1H,d); 8.11 (1H,d); 7.59–7.74 (3H,m); 7.15 (1H,d.t.); 7.05–7.1 (3H,m).

4-[4-Acetylamino-2-(3-nitrobenzoylamino)phenoxy] phthalic acid (Compound 90) was prepared according the method described above using N-(4-fluoro-3-nitrophenyl)-acetamide instead of o-fluoronitrobenzene. LC-MS: m/e 480 (MH⁺), 462 (MH⁺-H₂O).

¹H-NMR (D₆-DMSO) in ppm: δ 10.31 (1H,s); 10.12 (1H,s); 8.4 (1H,s); 8.31 (1H,d); 8.05 (1H,d); 7.89 (1H,s); 7.67 (1H,t); 7.62 (1H,d); 7.44 (1H,d); 7.1 (1H,d); 6.99 (1H, d.d.); 6.95 (1H,s).

4-[4-Methoxycarbonyl-2-(3-nitrobenzoylamino)phenoxy] phthalic acid (Compound 91) was prepared according the method described above using methyl 4-fluoro-3-nitrobenzoate instead of o-fluoronitrobenzene. LC-MS: m/e 481 (MH⁺), 463 (MH⁺-H₂O).

¹H-NMR (D₆-DMSO) in ppm: δ 10.50 (1H,s); 8.63 (1H,s); 8.42 (1H,d); 8.35 (1H,s); 8.24 (1H,d); 7.90 (1H,d.d.); 7.72–7.82 (2H,m); 7.18–7.26 (3H,m).

4-[4-(4-Iodobenzoylamino)-2-(3-nitrobenzoylamino) phenoxy]phthalic acid (Compound 92) was prepared according the method described above using N-(4-fluoro-3-nitrophenyl)-4-iodo-benzamide instead of o-fluoronitrobenzene. LC-MS: m/e 690 (M+Na), 668 (MH⁺), 650 (MH⁺-H₂O).

¹H-NMR (D₆-DMSO) in ppm: δ 10.47 (1H,s); 10.39 (1H,s); 8.56 (1H,s); 8.39 (1H,d); 8.15–8.21 (2H,m); 7.94 (2H,d); 7.68–7.8 (5H,mt); 7.22 (1H,d); 7.06–7.11 (2H,m).

Example 2

4-[2-(3-Aminobenzoylamino)phenoxy]phthalic acid (Compound 93)

100% acetic acid (250 μl) and palladium on activated charcoal (10% Pd, 40 mg) was added to a solution of 4-[2-(3-nitrobenzoylamino)phenoxy]phthalic acid (130 mg, 0.308 mmol) in methanol/water (10:1) (11 ml). The mixture was hydrogenated in a Parr apparatus at 276 kPa (40 psi) for 20 hours. The mixture was filtered and evaporated to dryness in vacuo to give 4-[2-(3-aminobenzoylamino)phenoxy] phthalic acid as an oil (yield: 114 mg (95%)). LC-MS: m/e 393 (MH⁺), 375 (MH⁺-H₂O).

Example 3

4-(2-Aminophenoxy)phthalonitrile

A mixture of 4-nitrophthalonitrile (0.6 g, 5.78 mmol), 2-aminophenol (1 g, 5.78 mmol) and potassium carbonate (1.6 g, 11.6 mmol) in DMF (25 ml) was stirred at room temperature for 2 hours. The mixture was then poured into water. The precipitate was filtered off, washed with water and dried to give yellow crystals of 4-(2-aminophenoxy) phthalonitrile (yield: 1.32 g (97%)). Mp: 118–118.2° C.

In a similar way the following compounds were prepared:

4-(3-Aminophenoxy)phthalonitrile from 4-nitrophthalonitrile (0.6 g, 5.78 mmol) and 3-aminophenol (1.0 g, 5.78 mmol). The product was recrystallised from methylene chloride/hexane to give 1.27 g (93%) of beige crystals. Mp: 171.2–172° C.

3-(2-Aminophenoxy)phthalonitrile from 4-nitrophthalonitrile (0.6 g, 5.78 mmol) and 2-aminophenol (1,0 g, 5.78 mmol). Evaporation in vacuo gave 1.16 g (85%) of beige crystals. Mp: 131.7–132° C.

4-(2-Nitrophenoxy)phthalonitrile from 4-nitrophthalonitrile (2.0 g, 11.5 mmol) and 2-nitrophenol (1.6 g, 11.5 mmol). The crude product was recrystallised from acetone/pentane to give 1.25 g (41%) of white crystals.

Example 4

4-(2-Aminophenylsulfenyl)phthalic acid dimethyl ester

Sodium hydride, 60% dispersion in mineral oil, (0.18 g, 4.5 mmol) was added to a solution of 2-aminothiophenol (0.59 ml, 4.0 mmol) in dry DMF (5 ml) at −20° C. The mixture was stirred at −20 to −30° C. for 10 minutes. A solution of 4-nitrophthalic acid dimethyl ester (0.83 g, 3.5 mmol) in dry DMF (5 ml) was added dropwise. The reaction mixture was stirred at −30° C.±5° C. for 1 hour and then at room temperature for 20 hours, poured into icewater (20 ml) and finally extracted with ethyl acetate (3×25 ml). The combined organic phase was washed with water (25 ml), dried over magnesium sulphate, and evaporated to dryness in vacuo. The crude product was purified on silica gel (eluent: methylene chloride) to give 4-(2-aminophenylsulfenyl)phthalic acid dimethyl ester (yield: 0.56 g (51%)) as a golden oil. ¹H—NMR (CDCl₃) in ppm: δ 3.85 (3H,s); 3.87 (3H,s); 4.29 (2H,broad s); 6.72–685 (2H,m); 7.07 (1H,d.d.); 7.23–7.34 (2H,m); 7.43 (1H,d.d.): 7.63 (1H,d).

In a similar way the following compound was prepared:

4-[Benzyl-(2-nitrophenyl)amino]phthalic acid dimethyl ester from 4-benzylaminophthalic acid dimethyl ester (0.8 g, 2.67 mmol) and o-fluoronitrobenzene (0.34 ml, 3.2 mmol). The crude product was purified on silica gel (eluent: methylene chloride) to give 4-[benzyl-(2-nitrophenyl)amino]phthalic acid dimethyl ester as an oil (yield: 0.57 g (51%)). ¹H—NMR (CDCl₃) in ppm: δ 3.74 (3H,s); 3.76 (3H,s); 4.75 (2H,s); 6.52–6.65 (2H,m); 7.15–7.26 (5H,m); 7.30–7.45 (2H,m); 7.53 (1H,d.d.); 7.60 (1H,d); 7.91 (1H,d).

Example 5

5-(2-Aminophenoxy)isoindole-1,3-dione 4-(2-Aminophenoxy)phthalonitrile (1.55 g, 6.6 mmol) was stirred with conc. sulphuric acid (9 ml) at room temperature for 15 hours. The mixture was purred into crushed ice and the pH was adjusted to 10 with diluted sodium hydrogencarbonate in water. The mixture was left for the weekend at room temperature. The resulting precipitate was filtered off and washed twice with water (2×50 ml). The crystals were dried to give yellow crystals of 5-(2-aminophenoxy)isoindole-1,3dione) (yield: 1.41 g (84%)). Mp: 211.6–211.9° C.

In a similar way the following compound was synthesized:

5-(2-Nitrophenoxy)isoindole-1,3-dione from 4-(2-nitrophenoxy)phthalonitrile (yield: 56% white crystals). LC/MS: m/e 285 (MH⁺).

Example 6

4-(2-Aminophenoxy)phthalamide 5-(2-Aminophenoxy)-isoindole-1,3-dione (0.1 g, 0.38 mmol) in conc. ammonium hydroxide (aq) was stirred at 60° C. for two hours. The reaction mixture was evaporated in vacuo (cold in order not to make the imide again). The crude mixture was used without any purification.

Example 7

N-[2-(3,4-Dicyanophenoxy)phenyl]acetamide (Compound 94)

4-(2-Aminophenoxy)phthalonitrile (0.54 g, 2.3 mmol) was stirred in acetic acid anhydride (20 ml) at room temperature for 1 hour. The reaction mixture was poured into crushed ice. The precipitate was filtered off and washed with water and dried in vacuo to give N-[2-(3,4-dicyanophenoxy)phenyl]acetamide as white crystals (yield: 0.57 g, (89%)). Mp: 152.2–153.7° C.

Example 8

2-[3-Cyano-4-(1H-tetrazol-5-yl)phenoxy]aniline or 2-[4-cyano-3-(1H-tetrazol-5-yl)phenoxy]aniline Ammonium chloride (0.46 g, 8.5 mmol) and sodium azide (0.55 g, 8.5 mmol) were added to a solution of 4-(2-aminophenoxy)phthalonitrile (0.5 g, 2.1 mmol) in DMF (20 ml). The reaction mixture was heated at 80° C. for 48 hours, cooled to room temperature and evaporated to dryness in vacuo. The crude compound was purified on silica gel (eluent: methylene chloride:methanol (4:1)) to give 2-[3-cyano-4-(1H-tetrazol-5yl)phenoxy]aniline or 2-[4-cyano-3-(1H-tetrazol-5-yl)phenoxy]aniline as yellow crystals (yield: 0.64 g (95%)). $^1$H—NMR (CD$_3$OD) in ppm: δ 5.2 (2H,s), 6.6 (1H, d,d), 6.85 (1H,d,d), 6.95 (1H,d,d.), 7.0 (1H,d,d.), 7.45 (1H,d), 7.65 (1H,d). $^{13}$C—NMR (CD$_3$OD) in ppm: δ 105.3; 118.7; 119.4; 119.7; 120.7; 123.0; 128.3; 133.3; 138.3; 138.3; 140.7; 142.8; 158.9; 163.4.

In a similar way the following compound was prepared: N-{2-[3-Cyano-4-(1-H-tetrazol-5-yl)phenoxy]phenyl}acetamide or N-{2-[4-cyano-3-(1H-tetrazol-5-yl)phenoxy]phenyl}acetamide (Compound 95) from N-[2-(3,4-dicyanophenoxy)phenyl]acetamide (0.55 g, 2.0 mmol), ammonium chloride (0.42 g, 8.0 mmol) and sodium azide (0.52 g, 8.0 mmol). The product was purified on silica gel (eluent: methylene chloride:methanol (4:1)) to give 0.55 g of a yellow foam. $^1$H—NMR (CD$_3$OD) in ppm: δ 2.0 (3H,s), 7.1 (1H,d), 7.15 (1H,d), 7.2–7.3 (2H,m), 7.07 (1H,d), 7.9 (1H,d), 8.0 (1H,s). $^{13}$C—NMR (CD$_3$OD) in ppm: δ 23.8; 106.1; 119.1; 119.3; 119.9; 122.7; 127.3; 127.4; 128.1; 131.9; 134.2; 138.2; 159.3; 165.3; 166.6; 172.6.

Example 9

4-Hydroxyphthalic acid dimethyl ester

Thionyl chloride (30 ml, 0.413 mmol) is added dropvise at −10° C. to a solution of 4-hydroxyphthalic acid (15 g, 82.4 mmol) in methanol (150 ml). The resulting mixture is heated at reflux temperature for 3 hours, cooled to room temperature and evaporated to dryness in vacuo to give 4-hydroxyphthalic acid dimethyl ester (yield: 17.1 g(99%)) as white crystals. $^1$H—NMR (CDCl$_3$) in ppm: δ 3.86 (3H,s), 3.92 (3H,s), 6.92 (1H,d,d.), 7.0 (1H,d), 7.76 (1H,d).

In a similar way the following compounds were prepared:
3-Hydroxyphthalic acid dimethyl ester from 3-hydroxyphthalic acid. $^1$H—NMR (CDCl$_3$) in ppm: δ 3.88 (3H,s); 3.92 (3H,s); 6.97 (1H,d.d.); 7.08 (1H,d.d.); 7.47 (1H,d.d.).
4-(Nitrophthalic acid dimethylester from 4-nitrophthalic acid. $^1$H—NMR (CDCl$_3$) in ppm: δ 3.98 (6H,2xs); 7.85 (1H,d.d.); 8.41 (1H,d.d.); 8.53 (1H,d.d.). Mp: 63.5–66° C.
4-Hydroxyisophthalic acid dimethyl ester from 4-hydroxyisophthalic acid. $^1$H—NMR (CDCl$_3$) in ppm: δ 3.92 (3H,s); 4.0 (3H,s); 7.04 (1H,d); 8.13 (1H,d.d.); 8.57 (1H,d).
4-(4-Nitrophenoxy)phthalic acid dimethyl ester from 4-(4-nitrophenoxy)phthalic acid. $^1$H—NMR (CDCl$_3$) in ppm: δ 3.94 (6H, 2xs); 7.1 (2H,d); 7.22 (1H, d.d.); 7.35 (1H,d); 7.87 (1H,d); 8.27 (2H,d).
4-Methylphthalic acid dimethyl ester from 4-methylphthalic acid. $^1$H—NMR (CDCl$_3$) in ppm: δ 2.4 (3H,s); 3.87 (3H,s); 3.90 (3H,s); 7.30 (1H,d); 7.46 (1H,s); 7.67 (1H,d).

Example 10

4-Aminophthalic acid dimethyl ester

Palladium on activated charcoal (10% Pd, 200 mg) was added to a solution of 4-nitrophthalic acid dimethyl ester (2.0 g, 8.37 mmol) in methylene chloride (100 ml). The mixture was hydrogenated in a Parr apparatus at 207 kPa (30 psi) for 1½ hour. The mixture was filtered and evaporated to dryness in vacuo to give 4-aminophthalic acid dimethyl ester as white crystals (yield: 1.75 g (100%)). Mp: 83–85° C. $^1$H—NMR (CDCl$_3$) in ppm: δ 3.80 (3H,s); 3.87 (3H,s); 6.6–6.7 (2H,m); 7.68 (1H,d).

Example 11

4-Benzylaminophthalic acid dimethyl ester

Benzaldehyde (1.64 ml, 16.2 mmol) and sodium cyanoborohydride (1.02 g, 16.2 mmol) were added to a solution of 4-aminophthalic acid dimethyl ester (1.7 g, 8.1 mmol) in dry methanol (50 ml) and pH was adjusted to 5.5–5 with 2 M hydrogen chloride in methanol (approx. 1 ml). The reaction mixture was stirred at room temperature for 20 hours and evaporated to dryness in vacuo. The residue was partitioned between methylene chloride (50 ml) and water (30 ml). pH was adjusted to 8 and the organic phase was isolated, dried over magnesium sulphate and evaporated to dryness in vacuo. The crude product was purified on silica gel (eluent: ether:heptane (1:1)) to give 4-benzylaminophthalic acid dimethyl ester as a golden oil (yield: 0.94 g, 39%). $^1$H—NMR (CDCl$_3$) in ppm: γ 3.82 (3H,s); 3.88 (3H,s); 4.35 (2H,d); 4.66 (1H, broad d); 6.57 (1H,d.d.); 6.65 (1H,d); 7.23–7.35 (5H,m); 7.73 (1H,d).

Example 12

4-(2-Nitrophenoxy)phthalic acid dimethyl ester

A mixture of 4-hydroxyphthalic acid dimethyl ester (1.23 g, 5.95 mmol), o-fluoronitro-benzene (0.81 ml, 7.64 mmol), and potassium carbonate (1.66 g, 12 mmol) in dry DMF (25 ml) was heated at 100° C. for 1 hour. The mixture was cooled to room temperature, filtered and the filtrate evaporated to dryness in vacuo to give 4-(2-nitrophenoxy)phthalic acid dimethyl ester as a yellow oil (yield: 1.97 g, (100%)). $^1$H—NMR (CDCl$_3$) in ppm: δ 3.9 (6H, 2xs); 7.1–7.2 (2H, m); 7.2 (1H,d); 7.3–7.4 (1H,m); 7.6–7.7 (1H,m); 7.84 (1H, d); 8.03 (1H, d.d.).

In a similar way the following compounds were prepared;
5-(2-Nitrophenoxy)isophthalic acid dimethyl ester from 5-hydroxyisophthalic acid dimethyl ester and o-fluoronitrobenzene. $^1$H—NMR (CDCl$_3$) in ppm: δ 3.95 (6H, s); 7.1 (2H,d.d.); 7.3–7.4 (1H,m); 7.55–7.65 (1H,m); 7.87 (2H,d); 8.03 (1H,d.d.); 8.5 (1H, d.d.).

4-(2-Nitrophenoxy)isophthalic acid dimethyl ester from 4-hydroxyisophthalic acid dimethyl ester and o-fluoronitrobenzene. $^1$H—NMR (CDCl$_3$) in ppm: δ 3.85 (3H,s); 3.95 (3H, s); 6.95–7.05 (2H,m); 7.25–7.35 (1H, m); 7.5–7.6 (1H,m); 8.03 (1H,d.d.); 8.17 (1H,d.d.); 8.65 (1H, d).

3-(2-Nitrophenoxy)phthalic acid dimethyl ester from 3-hydroxyphthalic acid dimethyl ester and o-fluoronitrobenzene. $^1$H—NMR (CDCl$_3$) in ppm: δ 3.92 (3H,s)l 3.96 (3H, s); 7.03 (1H,d.d.); 7.17 (1H,d.d.); 7.2–7.3 (1H,m); 7.4–7.6 (2H,m); 7.85 (1H,d.d.); 7.93 (1H,d.d.).

4-(2,4-Dinitrophenoxy)phthalic acid dimethyl ester from 4-hydroxyphthalic acid dimethyl ester (8.0 g) and 1-fluoro-2,4-dinitrobenzene (7.65 g). LC/MS: 345 (M+Na), 377 (MH$^+$).

Example 13

4-(2-Aminophenoxy)phthalic acid dimethyl ester

A mixture of 4-(2-nitrophenoxy)phthalic acid dimethyl ester (2.16 g, 6.53 mmol) and palladium on activated charcoal (10% Pd, 120 mg) in methylene chloride (115 ml) was hydrogenated in a Parr apparatus at 207 kPa (30 psi) for 16 hours. The mixture was filtered and evaporated to dryness in vacuo to give 4-(2-aminophenoxy)phthalic acid dimethyl ester as an yellow oil (yield: 1.88 g (96%)). $^1$H—NMR (CDCl$_3$) in ppm: δ 3.86 (3H,s); 3.90 (3H, s); 6.7–6.97 (3H,m); 7.0–7.1 ( 2H,m); 7.15 (1H,d); 7.78 (1H,d). $^{13}$C—NMR (CDCl$_3$) in ppm: δ 52.9; 53.2; 116.5; 117.4; 118.2; 119.4; 121.6; 124.4; 126.7; 132.1; 136.1; 139.2; 141.6; 160.8; 167.1; 168.8.

In a similar way the following compounds were prepared;
5-(2-Aminophenoxy)isophtalic acid dimethyl ester from 5-(2-nitrophenoxy)-isophtalic acid dimethyl ester. $^1$H—NMR (in CDCl$_3$): 3.95 (6H, s); 6.7–6.8 (1H,m); 6.8–6.9 (2H,m); 7.0–7.1 (1H,m); 7.8 (2H,d); 8.37 (1H,t).

4-(2-Aminophenoxy)isophtalic acid dimethyl ester from 4-(2-nitrophenoxy)-isophtalic acid dimethyl ester. $^1$H—NMR (CDCl$_3$) in ppm: δ 3.91 (3H,s); 3.94 (3H, s); 6.7–7.1 (5H,m); 8.03 (1H,d.d.); 8.53 (1H,d).

3-(2-Aminophenoxy)phthalic acid dimethyl ester from 3-(2-nitrophenoxy)phthalic acid dimethyl ester. $^1$H—NMR (CDCl$_3$) in ppm: δ 3.90 (3H,s); 3.97 (3H,s); 4.0–4.7 (NH$_2$,broad); 6.65–6.72 (2H, m); 6.94–7.08 (3H,m); 7.32 (1H,dd); 7.69 (1H,dd).

4-(4-Aminiophenoxy)phthalic acid dimethyl ester from 4-(4-nitrophenoxy)phthalic acid dimethyl ester. $^1$H—NMR (CDCl$_3$) in ppm: δ 3.90 (3H,s); 3.92 (3H, s); 6.7 (2H,d); 6.9 (2H,d): 7.02 (1H,d.d.); 7.07 (1H,d); 7.78 (1H,d).

4-(2,4-Diaminophenoxy)phthalic acid dimethyl ester from 4-(2,4-dinitrophenoxy)phthalic acid dimethyl ester. LC/MS: m/e 339 (M+NA), 317 (MH$^+$), 285.

Example 14

4-[(2-Aminophenyl)benzylamino]phthalic acid dimethyl ester

A clear solution of stannous chloride dihydrate (0.84 g, 3.72 mmol) in DMF (4ml) was added to a solution of 4-[benzyl-(2-nitrophenyl)amino]phthalic acid dimethyl ester (195 mg, 0.47 mmol) in DMF (4ml) and stirred for 3 hours at room temperature. The reaction mixture was poured into water and extracted with ethyl acetate (2×25 ml). The collected organic phases was washed with water (3×25 ml), dried over magnesium sulphate, and evaporated to dryness in vacuo to give 4-[(2-aminophenyl)benzylamino]phthalic acid dimethyl ester as a slightly coloured oil (yield: 180 mg (100%)).

Example 15

4-[2-(3-Nitrobenzoylamino)phenoxy]phthalic acid dimethyl ester (Compound 96)

A solution of 3-nitrobenzoyl chloride (0.43 g, 2.3 mmol) in dry acetone (2ml) was added slowly to a solution of 4-(2-aminophenoxy)phthalic acid dimethyl ester (0.63 g, 2.09 mmol) and TEA (0.35 ml, 2.5 mmol) in dry acetone (2ml) at 0° C. The mixture was stirred at room temperature for 20 hours, filtered and the filtrate evaporated to dryness in vacuo. The crude product was purified on silica gel (eluent: methylene chloride/ethyl acetate (95:5)) to give 4-[2-(3-nitrobenzoylamino)phenoxy]phthalic acid dimethyl ester (yield: 1.19 g (47%)) as a golden oil. $^1$H—NMR (CDCl$_3$) in ppm: δ 3.9 (6H,2xs); 7.02 (1H,d.d.); 7.1–7.25 (2H,m); 7.25–7.35 (2H,m); 7.7 (1H,t); 7.83 (1H,d); 8.1 (1H,d.t.); 8.3 (1H, broad s); 8.4 (1H,m); 8.54 (1H,d.d.); 8.65 (1H,m).

In a similar way the following compounds were prepared:
5-[2-(3-Nitrobenzoylamino)phenoxy]isophthalic acid dimethyl ester (Compound 97) from 5-(2-aminophenoxy)isophthalic acid dimethyl ester and 3-nitrobenzoyl chloride. $^1$H—NMR (CDCl$_3$) in ppm: δ 3.96 (6H,s); 6.9 (1H,d.d.); 7.15 (2H,d.t.); 7.25 (1H,d.t.); 7.68 (1H,t); 7.92 (1H,d); 8.16 (1H,d.t.); 8.35–8.41 (1H,m); 8.43 (1H,broad s); 8.5 (1H,m); 8.57 (1H,d.d.); 8.63 (1H,t).

4-[2-(3-Nitrobenzoylamino)phenoxy]isophthalic acid dimethyl ester (Compound 98) from 4-(2-aminophenoxy)isophthalic acid dimethyl ester and 3-nitrobenzoyl chloride. $^1$H—NMR (CDCl$_3$) in ppm: δ 3.9 (3H,s); 3.94 (3H,s); 7.1 (1H,d.); 7.2 (2H,m); 7.3–7.5 (1H,m); 7.64 (1H,t); 8.1 (1H,d.d.); 8.25–8.4 (2H,m); 8.55 (1H,d); 8.63 (1H,d); 8.7 (1H,m).

4-[4-(3-Nitrobenzoylamino)phenoxy]phthalic acid dimethyl ester (Compound 99) from 4-(4-aminophenoxy)phthalic acid dimethyl ester and 3-nitrobenzoyl chloride. $^1$H—NMR (CDCl$_3$) in ppm: δ 3.88 (6H,2xs); 7.0–7.2 (4H,m); 7.65–7.75 (3H,m); 1H,d); 8.3 (1H,d.t.); 8.4 (1H, d.m.); 8.5 (1H,broad s); 8.75 (1H,m).

3-[2-(3-Nitrobenzoylamino)phenoxy]phthalic acid dimethyl ester (Compound 100) from 3-(2-aminophenoxy)phthalic acid dimethyl ester and 3-nitrobenzoyl chloride. $^1$H—NMR (CDCl$_3$) in ppm: δ 3.90 (6H,2xs); 6.95–7.45 (5H,m); 7.55–7.75 (2H,m); 8.15 (1H,d.d.); 8.39 (1H,d.d.); 8.48 (1H,d.d.); 8.65 (1H,d.d.); 8.85 (1H,broad s). SP/MS: M+: 450.

4-[2-(3-Nitrobenzoylamino)phenylsulphenyl]phthalic acid dimethyl ester (Compound 101) from 4-(4-aminophenylsulphenyl)phthalic acid dimethyl ester and 3-nitrobenzoyl chloride. $^1$H—NMR (CDCl$_3$) in ppm: δ 3.85 (3H,s); 3.9 (3H,s); 7.15 (1H,d.d.); 7.3 (1H,m.t.); 7.4 (1H,d); 7.5–7.7 (4H,m); 8.0 (1H,d.m.); 8.36 (1H, d.m.); 8.53 (1H,t); 8.6 (1H,d.d.); 9.0 (1H,broad, s).

4-{Benzyl-[2-(3-nitrobenzoylamino)phenyl]amino}phthalic acid dimethyl ester (Compound 102) from 3-nitrobenzoyl chloride and 4-[(2-aminophenyl)benzylamino]phthalic acid dimethyl ester. LC-MS: m/e 540 (MH$^+$), 509

4-[2-(3-Nitrobenzoylamino)benzyl]phthalic acid dimethyl ester (Compound 103) from 3-nitrobenzoyl chloride and 4-(2-aminobenzyl)phthalic acid dimethyl ester. $^1$H—NMR (CDCl$_3$) in ppm: δ 3.85 (3H,s); 3.9 (3H,s); 4.14 (2H,s); 7.25–7.40 (4H,m); 7.43 (1H,d); 7.66 (4H,p); 7.90 (1H,d); 8.36 (1H,d.m.); 8.40 (1H,t). LC-MS: m/e 471 (M+Na), 449 (MH$^+$).

N-[2-(1,3-Dioxo-2,3-dihydro-1H-isoindol-5-yloxy)phenyl]-3-nitrobenzamide (Compound 104) from 5-(2-aminophenoxy)isoindole-1,3-dione (18 mg, 0.07 mmol) and 3-nitrobenzoylchloride (21 mg, 0.11 mmol). The reaction mixture was stirred at room temperature for 4 hours. The mixture was evaporated in vacuo and the residue was purified on silica gel to give N-[2-(1,3-dioxo-2,3-dihydro-1H-isoindol-5-yloxy)phenyl]-3-nitrobenzamide as white crystals (yield: 9 mg (32%)). LC-MS: m/e 404 (MH$^+$).

4-[2-(3-Trifluoromethylbenzoylamino)phenoxy]phthalic acid dimethyl ester (Compound 105) from 4-(2-aminophenoxy)phthalic acid dimethylester (100 mg) and 3-trifluoromethylbenzoyl chloride (68 mg) (yield: 120 mg (78%)). LC/MS: m/e 474 (MH$^+$).

4-{2-[(2-Chlorothiophene-3-carbonyl)amino]phenoxy}phthalic acid dimethyl ester (Compound 106) from 4-(2-aminophenoxy)phthalic acid dimethylester (100 mg) and 3-chloro-2-thiophene-carboxylic acid chloride (60 mg) (yield: 105 mg (71%)). LC/MS: m/e 446 (MH$^+$).

4-[2-(3-Trifluoromethoxybenzoylamino)phenoxy]phthalic acid dimethyl ester (Compound 107) from 4-(2-aminophenoxy)phthalic acid dimethylester (200 mg) and 3-trifluoromethoxybenzoyl chloride (137 mg).

4-[2-(3-Fluorobenzoylamino)phenoxy]phthalic acid dimethyl ester (Compound 108) from 4-(2-aminophenoxy)phthalic acid dimethylester (200 mg) and 3-fluorobenzoyl chloride (126 mg) (yield: 239 mg (85%). LC/MS: m/e: 446 (M+Na), 393.

4-[2-(3-Ethoxycarbonylbenzoylamino)phenoxy]phthalic acid dimethyl ester (Compound 109) from 4-(2-aminophenoxy)phthalic acid dimethylester (0.50 mg) and 3-ethoxycarbonylbenzoyl chloride (0.58 g) (yield: 0.64 g (100%). $^1$H—NMR (CDCl$_3$) in ppm: δ 1.4 (3H,t); 3.9 (6H,2xs); 4.40 (2H,q); 6.98 (1H,d.d.); 710–7.33 (4H,m); 7.56 (1H,t); 7.83 (1H,d); 7.97 (1H,d.m.); 8.20 (1H,d.m.); 8.30 (1H,broad s); 8.45 (1H,t); 8.60 (1H,d.d.).

4-[2-(3-Methoxycarbonylpropionylamino)phenoxy]phthalic acid dimethyl ester (Compound 110) from 4-(2-aminophenoxy)phthalic acid dimethylester (100 mg) and 3-methoxycarbonyl-propanoyl chloride (41 g) (yield: 91 g (80%). LC/MS: m/e 438 (M+Na), 384.

4-[2-(4-Methoxycarbonylbutyrylamino)phenoxy]phthalic acid dimethyl ester (Compound 111) from 4-(2-aminophenoxy)phthalic acid dimethylester (100 mg) and 4-methoxycarbonyl-butanoyl chloride (38 ml) (yield: 111 mg (95%). LC/MS: m/e 452 (M+Na), 430 (MH$^+$), 398.

4-[2-(3-Ethoxycarbonylacryloylamino)phenoxy]phthalic acid dimethyl ester (Compound 112) from 4-(2-aminophenoxy)phthalic acid dimethylester (200 mg) and 3-ethoxycarbonyl-propenoyl chloride (106 mg) (yield: 85 mg (36%)). LC/MS: m/z 450 (M+Na), 396.

4-[2,4-Bis-(2-bromo-4-nitrobenzoylamino)phenoxy] phthalic acid dimethyl ester (Compound 113) from 4-(2,4-diaminophenoxy)phthalic acid dimethyl ester (0.53 g) and 2-bromo-5-nitrobenzoyl chloride (1.0 g). The crude product purified on silica gel column (eluent: methylene chloride:methanol (5:1)) to give 4-([2,4-bis-(2-bromo-4-nitrobenzoylamino)phenoxy]phthalic acid dimethyl ester as brownish crystals (yield: 0.81 g 63%). Mp: 138–142° C. LC/MS: 794 (M+Na), 773 (MH$^+$), 740 (M—OMe). CHN: Calculated: C: 46.66; H: 2.61; N: 7.25; Br: 20.69. Found C: 47.05; H: 2.94; N: 6.85; Br: 20.22.

4-[4-(3-Nitrobenzoylamino)benzoyl]phthalic acid dimethyl ester (Compound 114) from 4-(4-aminophenoxy)phthalic acid dimethyl ester (250 mg) and 3-nitrobenzoyl chloride (148 mg) to give yellow crystals of 4-[4-(3-nitrobenzoylamino)benzoyl]phthalic acid dimethyl ester (yield: 350 mg 100%). Mp: 144–146° C. LC/MS: m/e 485 (M+Na), 463 (MH$^+$).

4-[2-(3-Nitrobenzoylamino)benzoyl]phthalic acid dimethyl ester (Compound 115) from 4-(2-aminobenzoyl)phthalic acid dimethyl ester (250 mg) and 3-nitrobenzoyl chloride (148 mg) to give 4-[2-(3-nitrobenzoylamino)benzoyl] phthalic acid dimethyl ester as yellow crystals (yield: 318 mg 85%)). Mp: 133–137° C. LC/MS: m/e 485 (M+Na), 463 (MH$^+$), 431.

4-[2-(3-Chloromethylbenzoylamino)phenoxy]phthalic acid dimethyl ester (Compound 116) from dimethyl-4-(2-aminophenoxy)phthalic (0.10 g, 0.27 mmol) and 3-chloromethylbenzoyl chloride (51 mg, 0.27 mmol) (yield: 96 mg 80%)). LC/MS: m/e 454 (M$^+$), 422.

N-{2-[3-Cyano-4-(1H-tetrazol-5-yl)phenoxyl]phenyl}-3-nitrobenzamide or N-{2-[4-cyano-3-(1H-tetrazol-5-yl)phenoxy]phenyl}-3-nitrobenzamide (Compound 117) from 5-(2-aminophenoxy)-2-(1H-tetrazol-5-yl)benzonitrile (0.15 g, 0.47 mmol) and 3-nitro-benzoyl chloride (95 mg, 0.51 mmol) (yield: 6 mg (3%)). $^1$H—NMR (acetone-d$_6$) in ppm: δ 7.3 (m,3H); 7.6 (t,2H); 7.9 (d,1H); 8.15 (m,1H); 8.25 (d,1H); 8.45 (d,1H); 8.6 (s,1H). LC/MS: m/e 428 (M+1).

Example 16

4-[2-(3-Nitrobenzoylamino)benzenesulfinyl]phthalic acid dimethyl ester (Compound 118)

3-Chloroperoxybenzoic acid, 70% (32.5 mg, 0.132 mmol) was added to a solution of 4-(2-aminophenylsulfenyl) phthalic acid dimethyl ester (60 mg, 0.129) in methylene chloride (1 ml). The mixture was stirred at room temperature for 1 hour, diluted with methylene chloride (2 ml) and with 10% aqueous sodium hydrogen carbonate (0.5 ml). The organic phase was isolated, dried over magnesium sulphate and evaporated to dryness in vacuo. The crude product was purified on silica gel (eluent: methylene chloride:ethyl acetate (90:10)) to give 4-[2-(3-nitrobenzoylamino)-benzenesulfinyl]phthalic acid dimethyl ester as a thick, colourless oil (yield: 29 mg (47%)). $^1$H—NMR (CDCl$_3$) in ppm: γ 3.80 (3H,s); 3.87 (3H,s); 7.33 (1H,d.t.): 7.55–7.80 (5H,m); 7.90 (1H,d); 8.30 (1H,d); 8.42 (1H, d.m.); 8.62 (1H,d); 8.8 (1H,t); 11.16 (1H,s).

In a similar way the following compound was prepared:
4-[2-(3-Nitrobenzoylamino)benzenesulfinyl]phthalic acid dimethyl ester (Compound 119) from 4-(2-aminophenylsulfenyl)phthalic acid dimethyl ester. $^1$H—NMR (CDCl$_3$) in ppm: δ 3.82 (3H,s); 3.90 (3H,s); 7.37 (1H,d.t.): 7.67–7.85 (2H,m); 7.96 (1H,d.d.); 8.06 (1H,d.d.); 8.24 (1H,d); 8.32 (1H,d.t.); 8.47 (1H,d.m.); 8.67 (1H,d.d.); 8.87 (1H,t); 10.8 (1H,s).

Example 17

4-[2-(3-Nitrobenzoylamino)phenoxy]phthalic acid dimethyl ester (Compound 120)

A solution of 3-(2-aminophenoxy)phthalic acid dimethyl ester (200 mg, 0.54 mmol) and 3-nitrobenzaldehyde (90 mg, 0.60 mmol) in toluen (20 ml) was refluxed for 30 hours with a Dean-Stark trap. The reaction mixture is cooled to room temperature and evaporated to dryness in vacuo. The residue was dissolved in methanol (5ml), sodium cyanoborohydride (100 mg, 1.58 mmol) was added, and pH adjusted to 4.5 by means of hydrogen chloride in ether. The mixture was stirred at room temperature for 20 hours, evaporated in dryness in vacuo, and partioned between methylene chloride (5 ml) and water (5 ml). The organic phase was isolated, dried over magnesium sulphate, and evaporated to dryness in vacuo. The crude compound was purified on silica gel (eluent: methylene chloride:ethyl acetate (95:5)) to give 4-[2-(3-nitrobenzylamino)phenoxy]phthalic acid dimethyl ester as a yellow oil (yield: 130 mg (55%). $^1$H—NMR (CDCl$_3$) in ppm: δ 8.05–8.18 (2H,m); 7.84 (1H,d); 7.63 (1H,d); 7.50 (1H,t); 7.20 (1H,d); 6.9–7.1 (3H,m); 6.73 (1H,d.t.); 6.6 (1H,d.d.); 4.56 (1H,broad, s): 4.48 (2H,broad s); 3.9 (3H,s); 3.87 (3H,s). LC-MS: m/e 459 (M+Na), 437 (MH$^+$).

Example 18

4-[2-(tert-Butoxycarbonylamino)benzyl]phthalic acid dimethyl ester

N-Bromosuccinimdie (4.3 g, 24.2 mmol) and benzoylp-eroxide (50 mg) was added to a solution of 4-methylphthalic acid dimethyl ester in carbon tetrachloride (50 ml). The mixture was heated to reflux temperature for two hours, cooled to room temperature and evaporated to dryness in vacuo to give 4-bromomethylphthalic acid dimethyl ester. The crude product was used in the next step without purification.

A mixture of 4-bromomethylphthalic acid dimethyl ester (3.1 g, 10.8 mmol), 2-(tert-butoxycarbonylamino) phenylboronic acid (4.3 g, 18.1 mmol), tetrakis (triphenylphosphine)-palladium(0) (0.6 g), 2 M aqueous sodium carbonate (20 ml), and 1,2-dimethoxyethane (40 ml) was heated at 90° C. for 19 hours. The reaction mixture was cooled to room temperature and partioned between water (60 ml) and methylene chloride (60 ml). The organic phase was isolated, washed with water (2×50 ml), dried over magnesium sulphate, and evaporated to dryness in vacuo. The crude product was purified on silica gel (eluent: methylene chloride:ethyl acetate (95:5) to give 4-[2-(tert-butoxycarbonylamino)benzyl]phthalic acid dimethyl ester as yellow crystals (yield: 1.49 g, (40%)). $^1$H—NMR (CDCl$_3$) in ppm: δ 7.70 (1H,d); 7.67 (1H,d); 7.47 (1H,d); 7.22–7.33 (2H,m); 7.10 (2H,d); 6.05 (1H,s); 4.03 (2H,s); 3.9 (6H,2xs); 1.47 (9H,s).

Example 19

4-(2-Aminobenzyl)phthalic acid dimethyl ester 2N hydrogen chloride in diethyl ether (1 ml) was added to a solution of 4-(2-(tert-butoxycarbonylamino)benzyl) phthalic acid dimethyl ester (100 mg, 0.25 mmol) in methanol (1 ml). The mixture was stirred for 2 hours at room temperature and evaporated to dryness in vacuo. The crude product was recrystallized from diethyl ether/ethyl acetate to give light, golden crystals of 4-(2-aminobenzyl)phthalic acid dimethyl ester (yield: 69 mg (86%)). $^1$H—NMR (CDCl$_3$) in ppm: δ 7.74 (1H,d); 7.60 (1H,s); 7.54 (1H,d); 7.27 (2H,d); 7.13 (1H,m); 7.05 (1H,d); 4.12 (2H,s); 3.8 (6H,2xs); 2.5 (3H,s). LC-MS: m/e 322 (M+Na), 300 (MH$^+$).

Example 20

4-[2-(3-Nitrobenzylamino)phenoxy]phthalic acid (Compound 1)

2N sodium hydroxide (12 ml) was added to a solution of 4-(2-(3-nitrobenzoylamino)-phenoxy)phthalic acid dimethylester (1.15 g, 2.83 mmol) in 1,4-dioxan (12 ml) at room temperature. The mixture was stirred for 2 hours, cooled to <10° C. and pH adjusted to 2–3 with 1N hydrochloric acid (approx. 24 ml). The resulting crystals were filtered off and washed with water. The crystals were dried to give beige crystals of 4-[2-(3-nitrobenzoylamino)-phenoxyl]phthalic acid (yield: 0.82 g. (76%)). $^1$H—NMR (CDCl$_3$) in ppm: δ 10.3 (s, 1H), 8.38 (m, 1H), 8.18 (d, 1H), 7.6–7.8 (m, 3H), 7.3–7.4 (m, 2H), 7.18 (d.d., 1H), 7.1 (m, 1H), 7.07 (d.d., 1H). Mp: 199.7–201.0° C.

In a similar way the following compounds were prepared:

5-[2-(3-Nitrobenzoylamino)phenoxy]isophthalic acid (Compound 121) from 5-[2-(3-nitrobenzoylamino) phenoxy]isophtalic acid dimethylester. Mp: 184–190° C.

4-[2-(3-Nitrobenzoylamino)phenoxy]isophthalic acid (Compound 122) from 4-[2-(3-nitrobenzoylamino) phenoxy]isophthalic acid dimethylester. Mp: 255–257° C.

4-[4-(3-Nitrobenzoylamino)phenoxy]phthalic acid (Compound 123) from 4-[4-(3-nitrobenzoylamino) phenoxy]phthalic acid dimethylester. Mp: 225–227° C.

3-[2-(3-Nitrobenzoylamino)phenoxy]phthalic acid (Compound 124) from 3-[2-(3-nitrobenzoylamino) phenoxy]phthalic acid dimethylester. LC-MS: m/e 423 (MH$^+$).

4-[2-(3-Nitrobenzoylamino)phenylsulphenyl]phthalic acid (Compound 125) from 4-[2-(3-nitrobenzoylamino) phenylsulphenyl]phthalic acid dimethylester. Mp: 172.8–173.9° C.

4-[2-(3-Nitrobenzoylamino)benzenesulfinyl]phthalic acid (Compound 126) from 4-[2-(3-nitrobenzoylamino) benzenesulfinyl]phthalic acid dimethylester. $^1$H—NMR (CDCl$_3$) in ppm: δ 8.8 (1H,t); 8.5 (1H,d.m.); 8.33 (1H, d.t.); 8.05 (1H,s); 7.86 (3H,t); 7.6–7.30 (3H,m); 7.50 (1H,d.t.). LC-MS: m/e 477 (M+Na), 455 (MH$^+$), 437 (MH$^+$–H$_2$O).

4-[2-(3-Nitrobenzoylamino)phenoxy]phthalic acid (Compound 127) from 4-[2-(3-nitrobenzoylamino) phenoxy]phthalic acid dimethylester. $^1$H—NMR (DMSO-d$_6$) in ppm: δ 8.18 (1H,s); 8.08 (1H,d); 7.77 (2H); 7.60 (1H,t); 7.04 (2H,s); 6.9–7.0 (2H,m); 6.57–6.67 (2H,m); 6.33 (1H,broad s); 4.50 (1H,s). LC-MS: m/e 431 (M+Na), 409 (MH$^+$), 391 (MH$^+$–H$_2$O).

4-{Benzyl-[2-(3-nitrobenzoylamino)phenyl]amino}phthalic acid (Compound 128) from 4-{benzyl-[2-(3-nitrobenzylamino(phenyl]amino}phthalic acid dimethyl ester. LC-MS: m/e 534 (M+Na), 512 (MH$^+$), 494 (MH$^+$–H$_2$O).

4-[2-(3-Nitrobenzoylamino)benzyl]phthalic acid (Compound 129) from 4-[2-(3-nitrobenzoylamino) benzyl]phthalic acid dimethyl ester. $^1$H—NMR (DMSO-d$_6$) in ppm: δ 13.0 (2H, broad s); 10.30 (1H,s); 8.66 (1H,s); 8.41 (1H,d.d.); 8.27 (1H,d); 7.80 (1H,t); 7.53 (1H,d); 7.26–7.37 (6H,m); 4.10 (2H,s). LC-MS: m/e 443 (M+Na), 421 (MH$^+$), 403 (MH$^+$–H$_2$O).

4-[2-(3-Trifluoromethylbenzoylamino)phenoxy]phthalic acid (Compound 130) from 4-[2-(3-trifluoromethylbenzoylamino)phenoxy]phthalic acid dimethyl ester. LC/MS: m/e 468 (M+Na), 428 (MH$^+$–H$_2$O).

4-{2-[(2-Chlorothiophene-3-carbonyl)amino] phenoxy}phthalic acid (Compound 131) from 4-{2-[(2-chlorothiophene-3-carbonyl)amino]phenoxy}phthalic acid dimethyl ester. LC/MS: m/e 401 (MH$^+$–H$_2$O).

4-[2-(3-Trifluoromethoxybenzoylamino)phenoxy]phthalic acid (Compound 132) from 4-[2-(3-trifluoromethoxybenzoylamino)phenoxy]phthalic acid dimethyl ester. LC/MS: m/e 462 (MH$^+$), 420.

4-[2-(3- Fluorobenzoylamino)phenoxy]phthalic (Compound 133) from 4-[2-(3-fluorobenzoylamino) phenoxy]phthalic acid dimethyl ester. LC/MS: m/e 418 (M+Na), 378 (MH$^+$–H$_2$O).

4-[2-(3-Carboxyphenylcarbamoyl)phenoxy]phthalic acid (Compound 134) from 4-[2-(3-ethoxycarbonylbenzoylamino)phenoxy]phthalic acid dimethyl ester. Mp: 202–208° C. LC/MS: m/e 467 (M+2Na), 404 (MH$^+$–H$_2$O).

4-[2-(3-Carboxypropionylamino)phenoxy]phthalic acid (Compound 135) from 4-[2-(3-methoxycarbonylpropionylamino)phenoxy]phthalic acid dimethyl ester. LC/MS: m/e 396 (M+Na), 356 (MH$^+$–H$_2$O).

4-[2-(4-Carboxybutyrylamino)phenoxy]phthalic acid (Compound 136) from 4-[2-(4-methoxycarbonylbutyrylamino)phenoxy]phthalic acid dimethyl ester. LC/MS: m/e 410 (M+Na), 388 (MH$^+$), 370 (MH$^+$–H$_2$O).

4-[2-(3-Carboxyacryloylamino)phenoxy]phthalic acid (Compound 137) from 4-[2-(3-ethoxycarbonyl-2-propenoylamino)phenoxy]phthalic acid dimethyl ester. LC/MS: m/e 394 (M+Na), 354 (MH$^+$–H$_2$O). $^{13}$C NMR (MeOH-d$_4$): 170.4; 169.0; 167.5; 163.9; 160.2; 147.3; 136.8; 134.4; 131.9; 131.8; 130.1; 126.9; 126.2; 125.5; 125.2; 120.7; 118.9; 117.4

4-[2-(3-Nitrobenzoylamino)benzoyl]phthalic acid (Compound 138) from 4-[2-(3-nitrobenzoylamino)-benzoyl]phthalic acid dimethyl ester. LC/MS: m/e 457 (M+Na), 417 (MH$^+$–H$_2$O).

4-[4-(3-Nitrobenzoylamino)benzoyl]phthalic acid (Compound 139) from 4-[4-(3-nitrobenzoylamino)-benzoyl]phthalic acid dimethyl ester. LC/MS: m/e 457 (M+Na), 435 (MH$^+$), 417 (MH$^+$–H$_2$O).

4-[2,4-Bis-(2-bromo-5-nitrobenzoylamino)phenoxy] phthalic acid (Compound 140) from 4-[2,4-bis-(2-bromo-4-nitrobenzoylamino)phenoxy]phthalic acid dimethyl ester. LC/MS: m/e 764/762/760 (M+NH$_4$$^+$), 729/727/725 (MH$^+$–H$_2$O). CHN: Calculated: C: 45.19; H: 2.17; N: 7.53; Br: 21.47. Found C: 44.52; H: 2.81; N: 6.96; Br: 20.43 (in accordance with the monohydrate). $^{13}$C NMR (MeOH-d$_4$): δ 171.3; 170.1; 167.2; 167.0; 161.9; 148.9; 148.7; 145.3; 141.4; 141.0; 138.2; 137.2; 136.2; 136.1; 133.3; 131.5; 128.4; 128.3; 127.1; 125.1; 123.2; 120.7; 119.7; 119.1; 118.0.

4-[2-(3-Chloromethylbenzoylamino)phenoxy]phthalic acid (Compound 141) from 4-[2-(3-chloromethylbenzoylamino)phenoxy]phthalic acid dimethyl ester. LC/MS: m/e 390 (M—HCl), 372 (M—HCl-H$_2$O).

Example 21

4'-Iodo-2-nitrodiphenyl ether

4-Iodophenol (1 g, 4.5 mmol) was dissolved in DMF (20 ml). 2-Fluoronitrobenzene (0.64 g, 4.5 mmol) and K$_2$CO$_3$ were added. The reaction mixture was refluxed at 160° C. for 4 hours. The reaction mixture was poured into ice and stirred for 1 hour. The precipitate was filtered off, washed with water, and dried in vacuo to give 4'-iodo-2-nitrodiphenyl ether as slightly beige crystals (yield: 1.31 g (85%)). Mp: 88.8–90.8° C.

In a similar way the following compound was synthesized:
3-Iodo-2'-nitrodiphenyl ether
3-Iodophenol (3.0 g, 13.6 mmol) was dissolved in DMF (20 ml) and 2-fluoronitrobenzene (1.92 g, 13.6 mmol) and K$_2$CO$_3$ (2.07 g, 15 mmol) were added. The reaction mixture was heated to 160° C. for 15 hours. The mixture was poured into ice and was stirred for 1 hour. The resulting oil was extracted with methylene chloride (4×100 ml). The organic phase was dried over magnesium sulphate and evaporated in vacuo (yield: 4.45 g (96%) yellow oil). $^1$H NMR (CDCl$_3$) in ppm: γ 85–7.1 (m, 3H), 7.25 (t,d.,1H); 7.4 (m,1H); 7.55 (m,1H); 7.95 (d.d.,1H).

Example 22

[4-(2-Nitrophenoxy)phenyl]phosphonic acid diethyl ester

4'-Iodo-2-nitrodiphenyl ether (0.3 g, 0.88 mmol) was melted at 150° C. under N$_2$, and phosphorous acid triethyl ester (0.175 g, 1.06 mmol) and NiCl$_2$ (6 mg, 0.044 mmol) were added. The mixture was stirred at 150° C. under N$_2$ for 3 hours. The mixture was cooled and water/methylene chloride was added. The water phase was extracted with methylene chloride (2×50 ml). The organic phase was dried with magnesium sulphate, filtered and evaporated in vacuo. The remaining brown oil was purified on a silica gel column (eluent: methylene chloride/methanol (39:1)) to give the title compound as a yellow oil (yield: 0.14 g (45%)). $^1$H—NMR (CDCl$_3$) in ppm: 1.3 (6H, t); 4.15 (4H, q); 7.05 (1H, d); 7.08 (1H, d); 7.15 (1H, dd); 7.35 (1H, d.t.); 7.62 (1H, d.t.); 7.8 (1H,d); 7.85(1H, d); 7.95 (1H, d.d.). $^{13}$C—NMR (CDCl$_3$) in ppm; 16.6; 16.8; 62.5; 62.6; 117.9; 118.3; 122.0; 122.9; 125.3; 125.9; 126.3; 134.3; 134.5; 135.0; 142.4; 149.1; 160.3; 160.4.

In a similar way the following compound was synthesized:
[3-(2-Nitrophenoxy)phenyl]phosphonic acid diethyl ester
3-Iodo-2'-nitrodiphenylether (4.45 g, 13 mmol) was heated to 150° C. under N$_2$, and phosphorous acid triethyl ester (4.33 g, 26.1 mmol) and NiCl$_2$ were added. The mixture was heated 2 hours to 150° C. under N$_2$. Further phosphorous acid triethyl ester (4.33 g, 26.1 mmol) and NiCl$_2$ were added and the reaction mixture was heated for 15 hours. After cooling to room temperature water and methylene chloride were added. The water phase was extracted with methylene chloride (2×50 ml). The organic phase was dried over magnesium sulphate and evaporated in vacuo. The residue was purified on a silica gel column (eluent; methylene chloride/methanol (39:1)) (yield: 2.28 g yellow oil (50%)). $^1$H—NMR (CDCl$_3$) in ppm: δ 1.3 (t,6H), 4.1 (q,4H); 7.05 (d.d.,1H); 7.3 (m,3H); 7.4–7.7 (m,3H); 8.0 (d.d.,1H).

Example 23

[4-(2-Aminophenoxy)phenyl]phosphonic acid diethyl ester

[4-(2-Nitrophenoxy)phenyl]phosphonic acid diethyl ester (140 mg, 0.4 mmol) was dissolved in methylene chloride and Pd/C 10% was added under N$_2$. The compound was reduced with H$_2$ in a Parr-apparatus at 207 kPa (30 psi) for 15 hours. The catalyst was filtered off and the organic phase was evaporated in vacuo. The remaining oil was purified on a silica gel column (eluent: methylene chloride/methanol (39.1)) to give the title compound as an oil (yield: 118 mg (92%)). $^1$H—NMR (CDCl$_3$(in ppm: 1.32 (6H,t); 3.8 (2H, broad s); 4.1 (4H,q); 6.7 (1H,d.t.); 6.85 (1H,d.d.); 6.9 (1H,d.d.); 7.0 (3H,m); 7.7 (1H, d); 7.85 (1H,d). $^{13}$C—NMR (CDCl$_3$) in ppm: 16.7 16.8; 62,4; 62,5; 116.5; 116.8; 117.2; 119.2; 119.9; 121.7; 123.8; 126.4; 134.2; 134.4; 139.5; 141.8; 161.6; 161.6.

In a similar way the following compound was synthesized;

[3-(2-Aminophenoxy)phenyl]phosphonic acid diethyl ester from [3-(2-nitrophenoxy)phenyl]phosphonic acid diethyl ester (2.28 g, 6.5 mmol) (yield: 0.77 g (37%) yellow oil) $^1$H—NMR (CDCl$_6$) in ppm: δ 1.25 (t.d.,6H); 3.9 (broad s,2H); 4.1 (m,4H); 6.65 (t.d., 1H); 6.8 (t.d.,2H); 6.95 (t.d., 1H); 7.1 (d.d., 1H); 7.3–7.55 (m,3H).

Example 24

{4-[2-(3-Nitrobenzoylamino)phenoxy] phenly}phosphonic acid diethyl ester (Compound 142)

[4-(2-Aminiophenoxy)phenyl]phosphonic acid diethyl ester (118 mg, 0.37 mmol) was dissolved in acetone (20 ml) and 3-nitrobenzoylchloride (7.5 mg, 0.40 mmol) and TEA (9.3 mg, 0.92 mmol) were added. The reaction mixture was stirred at room temperature for 72 hours. The reaction mixture was evaporated in vacuo and the residue was dissolved in methylene chloride/water (2×30 ml). The organic phase was dried over magnesium sulphate, filtered and evaporated in vacuo. The remaining yellow oil was purified on a silica gel column (eluent: methylene chloride/methanol (19:1)) to give the title compound as an oil (yield: 8.7 mg (50%)). $^1$H—NMR (CDCl$_3$ in ppm): 1.3 (6H,t); 4.05 (4H,q); 7 (1H,d.d.); 7.15 (2H,d.d.); 7.25 (2H,m); 7.6–7.85 (3H,m); 8.1 (1H,d.d.); 8.35 (1H,d.d.); 8.45 (1H,d.d.); 8.6 (2H,m). $^{13}$C—NMR (CDCl$_3$ in ppm): 16.6; 16.8; 62,5; 62,6; 117.9; 118.2; 119.7; 122.0; 122.6; 122.8; 125.4; 125.7; 125.8; 126.8; 129.6; 130.0; 130.4; 133.4; 134.4; 134.6; 136.7; 145.7; 148.7; 160.3; 160.4; 163.5.

In a similar way the following compound was synthesized.:

{3-[2-(3-Nitrobenzoylamino)phenoxy]phenyl}phosphonic acid diethyl ester (Compound 143) from [3-(2-aminophenoxy)phenyl]phosphonic acid diethyl ester (0.10 g, 0.31 mmol) and 3-nitrobenzoylchloride (69 mg, 0.37 mmol) (yield: 110 mg oil (75%)). $^1$H—NMR (CDCl$_3$) in ppm: δ 1.3 (t,6H); 4.1 (m,4H); 6.9 (d.d.,1H); 7.1–7.3 (m,3H); 7.45–7.8 (m,3H); 8.15 (d.t.,1H); 8.35 (d.d.,1H); 8.45 (d.d.,1H); 8.7 (m,2H).

Example 25

{4-[2-(3-Nitrobenzoylamino)phenoxy] phenyl}phosphonic acid (Compound 144)

{4-[2-(3-Nitrobenzoylamino)phenoxy] phenyl}phosphonic acid diethyl ester (5 mg, 0.11 mmol) was dissolved in methylene chloride (5 ml) and trimethysilylbromide (13 mg, 0.85 mmol) was added. The reaction mixture was stirred for 16 hours at room temperature. Water (5ml) was added and the mixture was stirred vigorously until precipitation of white crystals of {4-[2-(3-nitrobenzoylamino)phenoxy]phenyl}phosphonic acid. The crystals were filtered off and dried (yield: 40 mg (91%)). Mp: 255–257.0° C.

In a similar way the following compound was synthesized:

{3-[2-(3-Nitrobenzoylamino)phenoxyl]phenyl}phosphonic acid (Compound 145) from {3-[2-(3-nitrobenzoylamino) phenoxy]phenyl}phosphonic acid diethyl ester (110 mg, 0.234 mmol) (yield: 64 mg white crystals (66%)). Mp: 120.4–122.4° C. LC/MS: m/e 415 (M+1).

Example 26

4-(2-Chloro-6-nitrophenoxy)benzenesulfonic acid 2, 2-dimethyl-propyl ester

A solution of 4-(2-chloro-6-nitrophenoxy (benzenesulfonyl chloride (0.25 g, 0.72 mmol) and neopentyl alcohol (75 mg, 0.85 mmol) in dry pyridine (0.7 ml) was heated with stirring at 50° C. for 20 hours. Subsequent partitioning between methylene chloride and water, followed by isolation and evaporation of the organic phase gave the crude product, which was purified on silica gel (eluent: methylene chloride:methyl tert-butyl ether (10:1)) to give crystals of 4-(2-chloro-6-nitrophenoxy)-benzenesulfonic acid 2,2-dimethyl-propyl ester (yield: 266 mg (93%)). Mp: 111–112° C. MS: m/e 399 (M$^+$).

Example 27

4-(2-Amino-6-chlorophenoxy)benzenesulfonic acid 2,2-dimethyl-propyl ester 4-(2-chloro-6-nitrophenoxy)-benzenesulfonic acid 2,2-dimethyl-propyl ester (0.25 g, 0.63 mmol) was reduced for 2 days by means of PtO$_2$ (5 mg) at atm pressure in ethanol:methylene chloride (4:1) (5 ml). The reaction mixture was filtrated and evaporated to dryness in vacuo to give (2-amino-6-chlorophenoxy)benzenesulfonic acid, 2,2-dimethyl-propyl ester, which was used in the next step without purification (yield: 0.12 g (50%)). LC/MS: m/e 370 (M$^+$), 300.

Example 28

4-[2-Chloro-6-(3-nitrobenzoylamino)phenoxy] benzenesulfonic acid 2,2-dimethyl-propyl ester (Compound 146)

(2-Amino-6-chlorophenoxy)benzenesulfonic acid, 2,2-dimethyl-propyl ester (43 mg, 0.12 mmol) was dissolved in acetone (10 ml) and triethyl amine (20 µl) and 3-nitrobenzoyl chloride (26 mg, 0.14 mmol) was added. The reaction mixture was stirred at room temperature for 20 hours, filtered and the filtrate evaporated to dryness in vacuo to give 4-[2-chloro-6-(3-nitro-benzoylamino)phenoxy] benzenesulfonic acid 2,2-dimethyl-propyl ester as an oil (yield: 52 mg (86%)). LC/MS: m/e 449 (M-neopentyl).

Example 29

4-[2-Chloro-6-(3-nitrobenzoylamino)phenoxy] benzenesulfonic acid (Compound 147)

A mixture of 4-[2-chloro-6-(3-nitrobenzoylamino) phenoxy]benzenesulfonic acid 2,2-dimethyl-propyl ester (52 mg, 0.10 mmol) and tetraethyl ammonium chloride (54 mg, 0.5 mmol) in DMF (5 ml) was stirred at reflux temperature for 24 hours. The reaction mixture was evaporated and purified on preparative HPLC (Gilson semi-prep.column prep-NOVA-PaK®HRC18, 6 microM, 60 Å; Flow 15 ml/min Gradient: 5–100% MeCN in water (20 min)) to give 4-[2-chloro-6-(3-nitrobenzoylamino)phenoxy] benzenesulfonic acid (yield 22 mg (25%)). LC/MS: m/e 449 (M$^+$).

Example 30

Dimethyl 4-(2-aminophenoxy)phthalate (0.27 mmol) was dissolved in acetone (1.5 ml). Carboxylic acid chloride (0.27 mmol) and triethyl amine (0.15 ml) were added and the mixture shaken at room temperature for 20 hours. After centrifugation the supernatant was evaporated to dryness in vacuo. The resulting oils were used in the next step without further purification.

4N sodium hydroxide (1 ml) and dioxan (3ml) were added to the residues and the mixture was shaken at room temperature for 20 hours. The water layer was isolated and evaporated to dryness in vacuo. Water (0.8 ml) was added and pH was adjusted to 2–3 with 6N hydrochloric acid (approx. 0.9 ml). The mixture was extracted with ethyl acetate (1.5 ml) and the organic layer was isolated and evaporated to dryness in vacuo.

The following compounds were prepared using the this general parallel fashion methodology:

4-{2-[(2-Chloro-6-methylpyridine-4-carbonyl)amino] phenoxy}phthalic acid (Compound 148) from 2-chloro-6-methylpyridine-4-carbonyl chloride and dimethyl-4-(2-aminophenoxy)phthalate LC/MS: m/e 427/429 (MH$^+$), 409/411 (MH$^+$–H$_2$O).

4-{2-[(2-Chloropyridine-4-carbonyl)amino] phenoxy}phthalic acid (Compound 149) from 2-chloropyridine-4-carbonyl chloride and dimethyl-4-(2-aminophenoxy)-phthalate. LC/MS: m/e 417/414 (MH$^+$), 395/397 (MH$^+$–H$_2$O).

4-{2-[(2-p-Tolyloxypyridine-3-carbonyl)amino] phenoxy}phthalic acid (Compound 150) from 2-p-tolyloxypyridine-3-carbonyl chloride and dimethyl-4-(2-aminophenoxy)phthalate. LC/MS: m/e 485 (M), 467 (M–H$_2$O).

4-{2-[(2-Phenoxypyridine-3-carbonyl)amino] phenoxy}phthalic acid (Compound 151) from 2-phenoxypyridine-3-carbonyl chloride and dimethyl 4-(2-aminophenoxy)phthalate. LC/MS: m/e 471 (MH$^+$), 453 (MH$^+$–H$_2$O).

4-(2-{[2-(4-Chlorophenoxy)pyridine-3-carbonyl] amino}phenoxy)phthalic acid (Compound 152) from 2-(4-chlorophenoxy)pyridine-3-carbonyl chloride and dimethyl 4-(2-aminophenoxy)-phthalate. LC/MS: m/e 505/507 (MH$^+$), 487/489 (MH$^+$–H$_2$O).

4-[2-(3,4-Difluorobenzenesulfonlyamino)phenoxy]phthalic acid (Compound 153) from 3,4-difluorobenzenesulphonyl chloride and dimethyl 4-(2-aminophenoxy)phthalate. LC/MS: m/e 450 (MH$^+$), 432 (MH$^+$–H$_2$O).

4-[2-(4-Chlorobenzenesulfonylamino)phenoxy]phthalic acid (Compound 154) from 4-chlorobenzenesulphonyl chloride and dimethyl 4-(2-aminophenoxy)phthalate. LC/MS: m/e 447/449 (MH$^+$), 430/432 (MH$^+$–H$_2$O).

4-[2-(4-Trifluoromethylbenzenesulfonylamino)phenoxy] phthalic acid (Compound 155) from 4-trifluoromethylbenzenesulphonyl chloride and dimethyl 4-(2-aminophenoxy)phthalate. LC/MS: m/e 482 (MH$^+$), 464 (MH$^+$–H$_2$O).

4-[2-(4-Nitrobenzenesulfonylamino)phenoxy]phthalic acid (Compound 156) from 4-nitromethylbenzenesulphonyl chloride and dimethyl 4-(2-aminophenoxy)phthalate. LC/MS: m/e 459 (MH$^+$), 441 (MH$^+$–H$_2$O).

4-[2-(3-Carboxybenzenesulfonylamino)phenoxy]phthalic acid (Compound 157) from 3-chlorosulphonylbenzoic acid and dimethyl 4-(2-aminophenoxy)phthalate. LC/MS: m/e 458 (MH$^+$), 440 (MH$^+$–H$_2$O), 422.

4-[2-(4-Cyanobenzenesulfonylamino)phenoxy]phthalic acid (Compound 158) from 4-cyanobenzenesulphonyl chloride and dimethyl 4-(2-aminophenoxy)phthalate. LC/MS: m/e 439 (MH$^+$), 422 (MH$^+$–H$_2$O).

4-{2-[(2,5-Dichlorothiophene-3-carbonyl)amino] phenoxy}phthalic acid (Compound 159) from 2,5-dichlorothiophene-3-carbonyl chloride and dimethyl 4-(2-aminophenoxy)phthalate. LC/MS: m/e 452/454/456 (MH$^+$), 434/436/437 (MH$^+$–H$_2$O).

4-{2-[(5-Bromopyridine-3-carbonyl)amino] phenoxy}phthalic acid (Compound 160) from 3-bromopyridine-3-carbonyl chloride and dimethyl 4-(2-aminophenoxy)phthalate. LC/MS: m/e 459/457 (MH$^+$), 439/441 (MH$^+$–H$_2$O).

4-{2-[(5,6-Dichloropyridine-3-carbonyl)amino] phenoxy}phthalic acid (Compound 161) from 5,6-dichloropyridine-3-carbonyl chloride and dimethyl 4-(2-aminophenoxy)phthalate. LC/MS: m/e 447/449/451 (MH$^+$), 429/431/433 (MH$^+$–H$_2$O).

4-(2-{[3-Chloro-4-(propane-2-sulfonyl)thiophene-2-carbonyl]aminophenoxy)phthalic acid (Compound 162) from 3-Chloro-4-(isopropylsulphonyl)thiophene-2-carbonyl chloride and dimethyl 4-(2-aminophenoxy) phthalate. LC/MS: m/e 526/524 (MH$^+$), 508/506 (MH$^+$–H$_2$O).

4-[2-(4-Chloro-3-nitrobenzoylamino)phenoxy]phthalic acid (Compound 163) from 4-chloro-3-nitrobenzoyl chloride and dimethyl 4-(2-aminophenoxy)phthalate. LC/MS: m/e 459/457 (MH$^+$), 441/439 MH$^+$–H$_2$O).

4-[2-(4-Fluoro-3-trifluoromethylbenzoylamino)phenoxy] phthalic acid (Compound 164) from 4-fluoro-3-trifluoromethylbenzoyl chloride and dimethyl 4-(2-aminophenoxy)phthalate. LC/MS: m/e 464 (MH$^+$), 419 (MH$^+$–H$_2$O).

4-[2-(4-Methyl-3-nitrobenzoylamino)phenoxy]phthalic acid (Compound 165) from 4-methyl-3-nitrobenzoyl chloride and dimethyl 4-(2-aminophenoxy)phthalate. LC/MS: m/e 437 (MH$^+$), 419 (MH$^+$–H$_2$O).

Example 31

N-{2-[3,4-Bis-(1H-tetrazol-5-yl)phenoxy] phenyl}acetamide (Compound 166)

A mixture of N-{2-[3-cyano-4-(1H-tetrazol-5-yl) phenoxy]phenoxy}acetamide and N-{2-[4-cyano-3-(1H-tetrazol-5-yl)phenoxy]phenyl}acetamide (0.45 g, 1.4 mmol) was dissolved in dry DMF (20 ml). Ammonium chloride (0.17 g, 3.1 mmol), sodium azide (0.2 g, 3.1 mmol), and lithium chloride (0.13 g, 3.1 mmol) were added. The reaction mixture was heated at 120° C. for 120 hours. The reaction mixture was evaporated in vacuo and purified on a silica gel column (eluent:methylene chloride/methanol (2:1)). The yielded oil was used without any further purification in the next step.

Example 32

N-{2-[3,4-Bis-(1-benzyl-1H-tetrazol-5-yl)phenoxy] phenyl}acetamide (Compound 167)

N-{2-[3,4-(1H-tetrazol-5-yl)phenoxy]phenyl}acetamide (0.83 g, 2.3 mmol) was dissolved in dry DMF (20 ml). Potassium carbonate (1.26 g, 9.1 mmol) and benzylbromide (1.26 g, 9.1 mmol) were added and the mixture was stirred for 120 hours at room temperature. The reaction mixture was evaporated in vacuo and purified on preparative HPLC. Eluent acetonitrile/H$_2$O (65:35). N-{2-[3,4-Bis-(1-benzyl-1H-tetrazol-5-yl)phenoxy]phenyl}acetamide was isolated as an oil (yield: 40 mg (3%)). $^1$H-NMR (CDCl$_3$ in ppm): 2.2 (3H,s), 5.1 (4H, 2xs); 6.9 (1H, d,d); 7.1 (1H, d,d); 7.15–7.2 (2H, m); 7.25–7.35 (10H,m); 7.55 (1H,d); 7.65 (1H, broad s); 7.85 (1H,d); 8.45 (1H,d).

Example 33

2-[3,4-Bis-(1-benzyl-1H-tetrazol-5-yl)phenoxy] phenylamine

N-{2-[3,4-Bis-(1-benzyl-1H-tetrazol-5-yl)phenoxy] phenyl}acetamide (40 mg, 0.07 mmol) was dissolved in ethanol (10 ml). 4N hydrochloric acid (10 ml) was added and the reaction mixture was refluxed for 15 hours. The mixture was evaporated in vacuo and redissolved in methylene chloride and 0.5 N aqueous sodium hydroxide (1:1) (20 ml). The organic phase was dried over magnesium sulphate and evaporated in vacuo to give 2-[3,4-bis-(1-benzyl-1H-tetrazol-5-yl)phenoxy]phenylamine as an oil (yield: 37 mg (100%)). $^1$H-NMR (CDCl$_3$ in ppm): 3.9 (2H, broad s); 5.58 (4H, s); 6.75 (1H, d.d.); 6.85 (1H,d.d.); 6.9 (1H,d.d.); 7.0 (1H,d.d.); 7.1 (1H,d.d.); 7.2–7.4 (10H,m); 7.48 (1H,d); 7.8 (1H,d).

Example 31

N-{2-[3,4-Bis-(1-benzyl-1H-tetrazol-5-yl)phenoxy] phenyl}-3-nitrobenzamide (Compound 168)

2-[3,4-Bis-(1-benzyl-1H-tetrazol-5-yl)phenoxy] phenylamine (37 mg, 0.07 mmol) and TEA (19 mg, 0.18 mmol) were mixed in acetone (10 ml), and 3-nitrobenzoyl chloride (15 mg, 0.08 mmol) was added. The reaction mixture was stirred for 120 hours at room temperature. The reaction mixture was evaporated in vacuo to an oil. The oil was purified on a silica column with methylene chloride/ methanol (39:1) as eluent. The title compound was isolated as yellow oil (yield: 30 mg (62%). $^1$H-NMR (CDCl$_3$ in ppm): 5.6 (4H,2xs); 7.0 (1H,d,d); 7.15 (1H,d,d); 7.2 (1H,d,d); 7.25–7.4 (11H,m); 7.6 (1H,d,d); 7.73 (1H,d); 7.9 (1H,d); 8.1 (1H,d,d); 8.35 (1H,d,d); 8.45 (1H,broad s); 8.55 (1H,d,d); 8.7 (1H,d,d).

In a similar way the following compounds were prepared:

4-[2-(3,5-Dinitrobenzoylamino)phenoxy]phthalic acid dimethyl ester (Compound 169) from 4-(2-aminophenoxy) phthalic acid dimethyl ester, hydrochloride (50 mg, 0.14 mmol) and 3,5-dinitrobenzoyl chloride (35 mg, 0.15 mmol) as a yellow oil (yield: 24 mg (36%)). $^1$H-NMR (CDCl$_3$) in ppm: δ 3.85 (6H,s); 7.0 (1H,d.d.); 7.2 (1H, d.d.); 7.25–7.35 (2H,m); 7.72 (2H,d); 8.4 (1H,d.d.); 8.6 (1H,broad s); 8.95 (2H,d.d.); 9.1 (1H,d.d.).

4-{2-[2-(2-Nitrophenyl)acetylamino]phenoxy}phthalic acid dimethyl ester (Compound 170) from 4-(2-aminophenoxy)phthalic acid dimethyl ester, hydrochloride (50 mg, 0.25 mmol) and 2-nitrophenylacetyl chloride (91 mg, 0.25 mmol) (yield: 88 mg (76%)). $^1$H-NMR (CDCl$_3$) in ppm: δ 3.9 (6H,s); 6.9 (2H,d.d.); 7.05 (2H,m); 7.15 (1H,d.d.); 7.4 (2H,broad d); 7.55 (1H,d.d.); 7.7 (1H,d); 7.9 (1H,d); 8.15 (1H,broad s); 8.4 (1H,d). $^{13}$C-NMR (CDCl$_3$) in ppm: δ 42.4; 53.0; 53.3; 117.0; 118.5; 120,4; 122.1; 125.2; 125.4; 126.4; 129.1; 129.8; 130.0; 132.0; 133.3; 134.1; 135.8; 143.7; 149.0; 159.8; 167.0; 167.7; 168.2.

4-{2-[2-(4-Hydroxy-3-nitrophenyl)acetylamino] phenoxy}phthalic acid dimethyl ester (Compound 171) from 4-(2-aminophenoxy)phthalic acid dimethyl ester, hydrochloride (30 mg, 0.08 mmol) and 3-nitro-4-hydroxyphenylacetyl chloride (17.2 mg, 0.08 mmol) (yield: 30 mg (77%)). $^1$H-NMR (CDCl$_3$) in ppm: δ 3.65 (2H,s); 3.9 (6H,2xs); 6.8–7.15 (5H,m); 7.25 (1H,d.d.); 7.4 (1H,d.d.); 7.55 (1H,broad s); 7.75 (1H,d); 7.95 (1H,d); 8.4 (1H,d); 10.5 (1H,broad s).

4-{2-[2-(2-Chloro-5-nitrophenyl)-acetylamino] phenoxy}phthalic acid dimethyl ester (Compound 172) from 4-(2-aminophenoxy)phthalic acid dimethyl ester, hydrochloride (30 mg, 0.08 mmol) and 2-chloro-5-nitrophenylacetyl chloride (19.1 mg, 0.08 mmol) (yield: 37 mg (93%)). $^1$H-NMR (CDCl$_3$) in ppm: δ 3.95 (8H, broad d); 6.95 (2H,d.d.); 7.05 (1H,d); 7.1 (1H,d.d.); 7.2 (1H,d.d.); 7.45 (1H,d)7.45–7.75 (0.5H,m); 7.7 (1H,d); 7.75 (0.5 H, broad s); 8.0 (1H,d.d.); 8.2 (1H,d); 8.45 (1H,d.d.). $^{13}$C-NMR (CDCl$_3$) in ppm: δ 42.6; 53.0; 53.3; 117.0; 118.5; 120.3; 122.3; 124.2; 125.5; 125.7; 126.8; 130.5; 131.0; 132.1; 134.6; 136.0; 141.5; 143.9; 146.9; 159.7; 166.8; 166.9; 168.2.

Example 32

4-{2-[2-(2-Nitrophenyl)acetylamino] phenoxy}phthalic acid (Compound 173)

4-{2-[2-(2-Nitrophenyl)acetylamino]phenoxy}phthalic acid dimethyl ester (88 mg, 0.19 mmol) was dissolved in 2N sodium hydroxide:dioxide (1:1) (13 ml). The reaction mixture was stirred for 2 hours at room temperature. Then 10N hydrochloric acid was added until pH=1. The reaction mixture was extracted with ethyl acetate (3×30 ml). The ethyl acetate phase was dried with magnesium sulphate, filtered and evaporated in vacuo. To the remaining oil was added acetone and pentane and 4-{2-[2-(2-nitrophenyl) acetylamino]phenoxy}phthalic acid precipitated as white crystals (yield: 56 mg (71%)). Mp: 208.8–209.2° C. LC/MS: m/e 436 (MH$^+$), 418 (MH$^+$-H$_2$O).

In a similar way the following compounds were synthesized:

4-{2-[2-(4-Hydroxy-3-nitrophenyl)-acetylamino] phenoxy}phthalic acid (Compound 174) from 4-{2-[2-(4-hydroxy-3-nitrophenyl)acetylamino]phenoxy}phthalic acid dimethyl ester as yellow crystals (yield: 27 mg (96%)). Mp: 187.8–189.9° C. LC/MS: m/e 452 (MH$^+$), 435 (MH$^+$-H$_2$O).

4-{2-[2-(2-Chloro-5-nitrophenyl)acetylamino] phenoxy}phthalic acid (Compound 175) from 4-{2-[2-(2-chloro-5-nitrophenyl)acetylamino]phenoxy}phthalic acid dimethyl ester as white crystals (yield: 26 mg (74%)). Mp: 176–178.2° C. LC/MS: m/e 470 (MH$^+$), 453 (MH$^+$-H$_2$O).

Example 33

N-[2-(3,4-Dicyanophenoxy)phenyl]-3-nitrobenzamide (Compound 176)

A mixture of 4-(2-aminophenoxy)phthalonitrile (0.5 g, 2.1 mmol), 3-nitrobenzoylchloride (0.43 g, 2.3 mmol) and triethylamine (0.54 g, 0.74 ml, 5.3 mmol) in acetone (20 ml) was stirred for 2 hours at room temperature. The mixture was evaporated in vacuo. The crude product was dissolved in methylene chloride (25 ml) and water (25 ml) and 1N hydrochloric acid (1 ml) was added. The water phase was extracted with methylene chloride (2×15 ml). The combined organic phase was dried over magnesium sulphate, filtered and evaporated in vacuo giving 700 mg of the crude product. The product was recystallised in acetone/pentane to give white crystals of N-[2-(3,4-dicyanophenoxy)phenyl]-3-nitrobenzamide (yield: 650 mg (81%)). Mp: 176.5–178.1° C.

PHARMACOLOGICAL METHODS

Rat hepatocytes were isolated using a standard two step collagenase technique, and cultured onto collagen coated culture dishes for 72 hours in medium 199 with the addition of dexamethazone (0.1 mM); penicillin/Streptomycin ((100 u/100 mg)/ml) and insulin (1 nM). During the last 24 hours, the hepatocytes were cultured in the presence of high levels of insulin (5 nM) and glucose (15 mM), which result in the incorporation of glucose into glycogen. Therefore, at the time of the experiment, the cells mimic levers from fed animals.

Experiments were initiated after 48 hours of culture of 2 times wash of cells and addition of a 20 mM HEPES experimental buffer including balanced salts, but without glucose. The test compound was added simultaneously with the experimental buffer. To some cultures, glucagon (0.5 nM) was added after 10 minutes in order to stimulate glucose production from liver cells. The glucose released into the media, reflecting the glucose production of the liver cells, was measured 70 minutes after the start of the experiment and standardized to cellular DNA content.

Phosphorylase was either purchased from Sigma or extracted from pig livers according to Stalmans et. al. (Eur.J.Biochem. 49, 415 (1974)), which reference is hereby incorporated by reference. The activity of phosphorylase was determined as described by Bergmeyer (1983; in: Meth. of Enzymatic Analysis 2, 293–295, Weinheim, (ed.) Verlag Chemie), which reference is hereby incorporated by reference.

Compounds of the present invention shows their effect in lowering the glucagon mediated increase in plasma glucose.

What is claimed is:

1. A compound of formula (I):

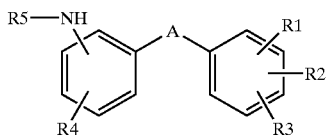

as well as any optical or geometric isomer or tautomeric form thereof and mixtures of these or a pharmaceutically acceptable basic organic or inorganic addition salt or hydrate or prodrug thereof, wherein
as well as any optical or geometric isomer or tautomeric form thereof and mixtures of these or a pharmaceutically acceptable basic organic or inorganic addition salt or hydrate or prodrug thereof, wherein A is —O—, —S—, >SO, >$SO_2$, >CO, >CR9R10, or >NR11;

R1 and R2 independently are one of the following groups: hydrogen, CN, —C(O)NR6R7, —COOH, —PO(OH)$_2$, —SO$_2$OH, tetrazole, 1-hydroxy-1,2-diazole, 1-hydroxytriazole, 1-hydroxyimidazole, 2-hydroxytriazole, or 1-hydroxytetrazole; when R1 or R2 is hydrogen, the other of R1 and R2 is —PO(OH)$_2$ or —SO$_2$OH; R1 and R2 together may form an anhydride or an imide;

R3 and R4 independently are $C_{1-8}$-alkyl, $C_{2-8}$-alkenyl, $C_{2-8}$-alkynyl, or $C_{3-8}$-cycloalkyl, each optionally substituted with halogen, hydroxy, —SH, —SOR6, —SO$_2$R6, —NR6R7, —NHCOR7, $C_{1-8}$-alkoxy, NO$_2$, trifluoromethoxy, carbamoyl, or —CONR6R7; or R3 or R4 independently are hydrogen, halogen, perhalomethyl, $C_{1-8}$-alkoxy, $C_{1-8}$-alkylthio, —SH, —SOR6, —SO$_2$R6, trifluoromethoxy, —SO$_2$OH, —PO(OH)$_2$, —COOR6, —CN, hydroxy, —OCOR6, —NR6R7, —NHCOR7, —COC$_{1-8}$-alkyl, —CONR6R7, —CONHSO$_2$R7, —SO$_2$NHR7, NO$_2$, $C_{1-8}$-alkoxycarbonyl, aryl, heteroaryl, $C_{1-8}$-alkylphenyl, or tetrazole;

R5 is —CO—R8; wherein R8 is aryl or heteroaryl, each optionally substituted with one or more substituents selected from halogen, hydroxy, —SH, —SOR6, —SO$_2$R6, NO$_2$, —NR6R7, —NHCOR7, $C_{1-8}$-alkyl, $C_{1-8}$-alkoxy, perhalomethoxy, carbamoyl, —CONR6R7, perhalomethyl, —OCOR6, —CO—R6, —OR6, $C_{1-8}$-alkylthio, —SO$_2$OH, —SO$_2$CH$_3$, —PO (OH)$_2$, CN, —NHCOR7, —CONHSO$_2$R7,
—SO$_2$NHR7, $C_{1-8}$-alkoxycarbonyl, and tetrazole; wherein R6 and R7 independently are hydrogen, $C_{1-8}$-alkyl, aryl, phenyl-$C_{1-8}$-alkyl, or heteroaryl, each optionally substituted with one or more substituents selected from halogen, OH, NH$_2$, NO$_2$, —NH($C_{1-8}$-alkyl), —N($C_{1-8}$-alkyl)$_2$, —NHCO($C_{1-8}$-alkyl), $C_{1-8}$-alkoxy, and trifluoromethoxy;

R9 and R10 independently are hydrogen, hydroxy, —SH, halogen, or $C_{1-8}$-alkyl; and R11 is hydrogen, $C_{1-8}$-alkyl, -carbonyl-$C_{1-8}$-alkyl, or phenyl $C_{1-8}$-alkyl.

2. A compound according to claim 1, wherein A is —O— or —S—.

3. A compound according to claim 2, wherein A is —O—.

4. A compound according to claim 1, wherein R1 and R2 both are —COOH or CN, or R1 and R2 together form an imide.

5. A compound according to claim 1, wherein R3 is hydrogen.

6. A compound according to claim 1, wherein R8 is aryl optionally substituted with one or more substituents selected from halogen, hydroxy, —SH, —SOR6, —SO$_2$R6, NO$_2$, —NR6R7, —NHCOR7, $C_{1-8}$-alkyl, $C_{1-8}$-alkoxy, perhalomethoxy, carbamoyl, —CONR6R7, perhalomethyl, —OCOR6, —CO—R6, —OR6, $C_{1-8}$-alkylthio, —SO$_2$OH, —SO$_2$CH$_3$, —PO(OH)$_2$, CN, —NHCOR7, —CONHSO$_2$R7, —SO$_2$NHR7, $C_{1-8}$-alkoxycarbonyl, or tetrazole.

7. A compound according to claim 6, wherein R8 is aryl optionally substituted with one or more substituents selected from halogen, NO$_2$, —SO$_2$CH$_3$, CN, $C_{1-8}$-alkyl, perhalomethyl, $C_{1-8}$-alkoxy, perhalomethoxy, $C_{1-8}$-alkylthio, —CO—R6, —NR6R7, —NH—CO—R7, and —OR6.

8. A compound according to claim 7, wherein R8 is aryl optionally substituted with one or more substituents and at least one of the substituents is NO$_2$.

9. A compound according to claim 1 which is
4-[2-(3-dimethylaminobenzoylamino)phenoxy]phthalic acid,
4-[2-(3-dimethylaminobenzoylamino)phenoxy]phthalic acid dimethyl ester,
4-[2-(3-iodobenzoylamino)phenoxy]phthalic acid,
4-[2-(3-iodobenzoylamino)phenoxy]phthalic acid dimethyl ester,
4-[2-(2-fluoro-5-trifluoromethylbenzoylamino)phenoxy] phthalic acid,
4-[2-(2-fluoro-5-trifluoromethylbenzoylamino)phenoxy] phthalic acid dimethyl ester,
4-[2-(2-fluorobenzoylamino)phenoxy]phthalic acid,
4-[2-(2-fluorobenzoylamino)phenoxy]phthalic acid dimethyl ester,
4-[2-(3-acetylbenzoylamino)phenoxy]phthalic acid,
4-[2-(3-acetylbenzoylamino)phenoxy]phthalic acid dimethyl ester,
4-[2-(3-bromobenzoylamino)phenoxy]phthalic acid,
4-[2-(3-bromobenzoylamino)phenoxy]phthalic acid dimethyl ester,
4-[2-(3-chlorobenzoylamino)phenoxy]phthalic acid,
4-[2-(3-chlorobenzoylamino)phenoxy]phthalic acid dimethyl ester,
4-[2-(2,3-difluorobenzoylamino)phenoxy]phthalic acid,
4-[2-(2,3-difluorobenzoylamino)phenoxy]phthalic acid dimethyl ester,
4-[2-(2,4-difluorobenzoylamino)phenoxy]phthalic acid,
4-[2-(2,4-difluorobenzoylamino)phenoxy]phthalic acid dimethyl ester, 4-[2-(2,5-difluorobenzoylamino)phenoxy]phthalic acid,
4-[2-(2,5-difluorobenzoylamino)phenoxy]phthalic acid dimethyl ester,
4-[2-(4-fluorobenzoylamino)phenoxy]phthalic acid,
4-[2-(4-fluorobenzoylamino)phenoxy]phthalic acid dimethyl ester,
4-(2-benzoylaminophenoxy)phthalic acid,
4-(2-benzoylaminophenoxy)phthalic acid dimethyl ester,
4-[2-(3-methylbenzoylamino)phenoxy]phthalic acid,
4-[2-(3-methylbenzoylamino)phenoxy]phthalic acid dimethyl ester,
4-[2-(3-cyanobenzoylamino)phenoxy]phthalic acid,
4-[2-(3-cyanobenzoylamino)phenoxy]phthalic acid dimethyl ester,
4-[4-amino-2-(3-nitrobenzoylamino)phenoxy]phthalic acid,
4-[4-amino-2-(3-nitrobenzoylamino)phenoxy]phthalic acid dimethyl ester,
N-[2-(1,3-dioxo-2,3-dihydro-1H-isoindol-5-yloxy)phenyl]-3-nitrobenzamide,
4-[2-(3-aminobenzoylamino)phenoxy]phthalic acid,
4-[2-(3-aminobenzoylamino)phenoxy]phthalic acid dimethyl ester,
4-[4-(3-nitrobenzoylamino)phenoxy]phthalic acid,
4-[4-(3-nitrobenzoylamino)phenoxy]phthalic acid dimethyl ester,
4-[2-(3-nitrobenzoylamino)phenoxy]phthalic acid,
4-[2-(3-nitrobenzoylamino)phenylsuphenyl]phthalic acid dimethyl ester,
4-[2-(3-nitrobenzoylamino)phenoxy]phthalic acid,
4-[2-(3-nitrobenzoylamino)phenoxy]phthalic acid dimethyl ester,
4-[4-(4-iodobenzoylamino)-2-(3-nitrobenzoylamino)phenoxy]phthalic acid,
4-[4-(4-iodobenzoylamino)-2-(3-nitrobenzoylamino)phenoxy]phthalic acid dimethyl ester,
4-[4-methoxycarbonyl-2-(3-nitrobenzoylamino)phenoxy]phthalic acid,
4-[4-methoxycarbonyl-2-(3-nitrobenzoylamino)phenoxy]phthalic acid dimethyl ester,
4-[4-acetylamino-2-(3-nitrobenzoylamino)phenoxy]phthalic acid,
4-[4-acetylamino-2-(3-nitrobenzoylamino)phenoxy]phthalic acid dimethyl ester,
4-[5-fluoro-2-(3-nitrobenzoylamino)phenoxy]phthalic acid,
4-[5-fluoro-2-(3-nitrobenzoylamino)phenoxy]phthalic acid dimethyl ester,
4-[4-bromo-2-(3-nitrobenzoylamino)phenoxy]phthalic acid,
4-[4-bromo-2-(3-nitrobenzoylamino)phenoxy]phthalic acid dimethyl ester,
4-[4-benzoylamino-2-(3-nitrobenzoylamino)phenoxy]phthalic acid,
4-[4-benzoylamino-2-(3-nitrobenzoylamino)phenoxy]phthalic acid dimethyl ester,
4-[5-methyl-2,4-bis-(3-nitrobenzoylamino)phenoxy]phthalic acid,
4-[5-methyl-2,4-bis-(3-nitrobenzoylamino)phenoxy]phthalic acid dimethyl ester,
4-[4-cyano-2-(3-nitrobenzoylamino)phenoxy]phthalic acid,
4-[4-cyano-2-(3-nitrobenzoylamino)phenoxy]phthalic acid dimethyl ester,
4-[4,5-dichloro-2-(3-nitrobenzoylamino)phenoxy]phthalic acid,
4-[4,5-dichloro-2-(3-nitrobenzoylamino)phenoxy]phthalic acid dimethyl ester,
4-[5-bromo-4-fluoro-2-(3-nitrobenzoylamino)phenoxy]phthalic acid,
4-[5-bromo-4-fluoro-2-(3-nitrobenzoylamino)phenoxy]phthalic acid dimethyl ester,
4-[4-methyl-2-(3-nitrobenzoylamino)phenoxy]phthalic acid,
4-[4-methyl-2-(3-nitrobenzoylamino)phenoxy]phthalic acid dimethyl ester,
4-[4-fluoro-2-(3-nitrobenzoylamino)phenoxy]phthalic acid,
4-[4-fluoro-2-(3-nitrobenzoylamino)phenoxy]phthalic acid dimethyl ester,
4-[5-methyl-2-(3-nitrobenzoylamino)phenoxy]phthalic acid,
4-[5-methyl-2-(3-nitrobenzoylamino)phenoxy]phthalic acid dimethyl ester,
4-[2-(3-nitrobenzoylamino)-4-trifluoromethylphenoxy]phthalic acid,
4-[2-(3-nitrobenzoylamino)-4-trifluoromethylphenoxy]phthalic acid dimethyl ester,
4-[2,4-bis-(3-nitrobenzoylamino)phenoxy]phthalic acid,
4-[2,4-bis-(3-nitrobenzoylamino)phenoxy]phthalic acid dimethyl ester,
4-[2-(3-nitrobenzoylamino)benzyl]phthalic acid,
4-[2-(3-nitrobenzoylamino)benzyl]phthalic acid dimethyl ester,
4-[2-(3-fluorobenzoylamino)phenoxy]phthalic acid,
4-[2-(3-fluorobenzoylamino)phenoxy]phthalic acid dimethyl ester,
4-[2-(3-trifluoromethylbenzoylamino)phenoxy]phthalic acid,
4-[2-(3-trifluoromethylbenzoylamino)phenoxy]phthalic acid dimethyl ester,
4-[2-(3-nitrobenzylamino)phenoxy]phthalic acid,
4-[2-(3-nitrobenzylamino)phenoxy]phthalic acid dimethyl ester,
4-[2-(3-trifluoromethoxybenzoylamino)phenoxy]phthalic acid,
4-[2-(3-trifluoromethoxybenzoylamino)phenoxy]phthalic acid dimethyl ester,
4-(benzyl-[2-(3-nitrobenzoylamino)phenyl]amino)phthalic acid,
4-(benzyl-[2-(3-nitrobenzoylamino)phenyl]amino)phthalic acid dimethyl ester,
4-[2-(3-nitrobenzoylamino)phenoxy]phthalic acid,
4-[2-(3-nitrobenzoylamino)phenoxy]phthalic acid dimethyl ester,
4-[2-(3-methoxybenzoylamino)phenoxy]phthalic acid, or
4-[2-(3-methoxybenzoylamino)phenoxy]phthalic acid dimethyl ester.

* * * * *